(12) United States Patent
Savoy et al.

(10) Patent No.: US 6,284,508 B1
(45) Date of Patent: Sep. 4, 2001

(54) GLUCURONOXYLOMANNAN (GXM)-O-ACETYLHYDROLASE OF *CRYPTOCOCCUS NEOFORMANS* AND USES THEREOF

(75) Inventors: Anne C. Savoy, Jacksonville, FL (US); Sherri L. Bloomer, Sparks; Thomas R. Kozel, Reno, both of NV (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/648,386

(22) Filed: Aug. 25, 2000

Related U.S. Application Data

(62) Division of application No. 09/371,710, filed on Aug. 9, 1999, now Pat. No. 6,146,868.

(51) Int. Cl.[7] .................................................. C12N 9/18
(52) U.S. Cl. ................................................................ 435/197
(58) Field of Search ..................................... 435/197, 975

(56) References Cited

PUBLICATIONS

Gadebusch, H.H, et al.(1961) Can. J. Microbiol.7, 53–60.*
Hattori, M., et al. (1995) J. Biol. Chem. 270(52), 31, 345–31,352.*
Albrecht, U., et al. (1996) Dev. Biol. 180, 579–593.*
Adachi, H., et al. (1997) Biochem. Biophys. Res. Com. 233, 10–13.*
Watanabe, M., et al. (1998) Biochim. Biophys. Acta 1401, 73–79.*

* cited by examiner

*Primary Examiner*—Charles L. Patterson, Jr.
(74) *Attorney, Agent, or Firm*—Benjamin Aaaron Adler

(57) ABSTRACT

The present invention provides a novel enzyme which de-O-acetylates glucuronoxylomannan of *Cryptococcus neoformans* and a gene encoding such enzyme. Also provided are applications of such enzyme in treating cryptococcosis.

5 Claims, 29 Drawing Sheets

| A | E | T | I | Y | Q | D | P | V | P | A | G | A | N | R | A | A | 17 |
|---|---|---|---|---|---|---|---|---|---|---|---|---|---|---|---|---|---|
|   |   |   |   |   |   | GAT | TGG | TAT | CGC | GAC | GTG | CAG | AAC | AAA | TTC | GAC | 33 |
|   |   |   |   |   |   | D | W | Y | R | D | V | Q | N | K | F | D | 34 |
| AAG | TAC | AGC | GGC | AAG | CCT | GCC | GAT | ATC | GTA | TTT | GAA | GGG | GAT | TCC | ATC | ACC | 84 |
| K | Y | S | G | K | P | A | D | I | V | F | E | G | D | S | I | T | 51 |
| AAC | CGC | TGG | GAA | ACG | GGC | AAA | GCG | GTS | TGG | AAG | GAA | CAT | TTT | GAA | GGT | 135 |
| N | R | W | E | T | G | K | A | V | W | K | E | H | F | E | G | 68 |
| CGT | GCC | GCG | GAT | TTC | GGM | ATC | GAG | GAC | GGC | GAC | GTG | GAA | AAT | GCG | TTG | TGG | 186 |
| R | A | A | D | F | G | I | E | D | G | D | V | E | N | A | L | W | 85 |
| CGG | TTG | AGC | AAG | GGA | CAG | GTG | GAT | GAC | ATT | AAC | CCA | AAA | GTG | GTC | ATC | 237 |
| R | L | S | K | G | Q | V | D | D | I | N | P | K | V | V | I | 102 |
| ATG | CTG | GGT | ACC | AAT | AAC | ACC | TAT | TTC | AAC | AGC | GCG | GAA | CAA | ATC | GCG | GAA | 288 |
| M | L | G | T | N | N | T | Y | F | N | S | A | E | Q | I | A | E | 119 |
| GGA | TTG | AAG | CTG | GTG | CTG | GTT | GCG | GAA | TAC | CAG | CGC | TGT | CCG | CAG | GCA | CAC | 339 |
| G | L | K | L | V | L | V | A | E | Y | Q | R | C | P | Q | A | H | 136 |
| ATC | ATC | CTG | ATG | GCG | TTC | CCG | CGC | AAA | AGC | CGC | GGC | GAC | GCT | AAC | GAT | GGC | GGT | 390 |
| I | I | L | M | A | F | P | R | K | S | R | G | D | A | N | D | G | 153 |
| CGC | AAG | AAG | GTA | TCG | TTC | GTG | GAA | ATC | AAT | AAG | ATC | AGC | GAC | ATC | TCC | CGC | GCC | GAC | 441 |
| R | K | K | V | S | F | V | E | I | N | K | I | S | D | I | S | R | A | D | 170 |
| GAC | AAG | ATC | CTG | ATG | GCG | TTC | GAT | AAG | ATG | ATC | CAG | CCC | GAC | GGC | 492 |
| D | K | I | L | M | A | F | D | K | M | I | Q | P | D | G | 187 |
| ACC | ATC | TCG | ACC | GAC | ATG | ATG | CCG | GAT | TTT | GTC | CAT | CCG | ACC | GCC | AAA | GGC | 543 |
| T | I | S | T | D | M | M | P | D | F | V | H | P | T | A | K | G | 204 |
| TAC | GAG | ATT | TGG | GGA | GAC | | | | | | | | | | | | 561 |
| Y | E | I | W | G | D | A | I | L | P | I | N | N | | | | | 217 |

Fig. 9B

```
CCA GTA CCC GGG GAT TAA TCA AAT GGA AAA ATC ATG AAT AAA CTG CAT CTT    18
                                            M   N   K   L   H   L      6

GTC ATT AGC GTT CAA CTG TTA GCC GTT GCC GGT TCG TTG TTA GCG GCG GAA    69
 V   I   S   V   Q   L   L   A   V   A   G   S   L   L   A   A   E    23

ACC ATC TAT CAG GAT CCT GTT CCA GCG GGT GCC AAC CGT GCT GCC GTT GCC   120
 T   I   Y   Q   D   P   V   P   A   G   A   N   R   A   A   V   A    40

GTC CCG CGC AAC GAT TGG TAT CGC GAC GTG CAG AAC AAA TTC GAC AAG TAC   171
 V   P   R   N   D   W   Y   R   D   V   Q   N   K   F   D   K   Y    57

AGC GGC AAG CCT GCC GAT ATC GTA TTT GAA GGG GAT TCC ATC ACC AAC CGC   222
 S   G   K   P   A   D   I   V   F   E   G   D   S   I   T   N   R    74

TGG GAA GGC ACG GGC AAA GCG GTS TGG AAG GAA CAT TTT GAA GGT CGT GCC   273
 W   E   G   T   G   K   A   V   W   K   E   H   F   E   G   R   A    91
```

Fig. 12A

```
GCG GAT TTC GGM ATC GAG GGC GAC CGC GTG GAA AAT GCG TTG TGG CGG TTG  324
 A   D   F   G   I   E   G   D   R   V   E   N   A   L   W   R   L   108

AGC AAG GGA CAG GTG GAT GAC ATT AAC CCA AAA GTG GTC ATC ATG CTG  375
 S   K   G   Q   V   D   D   I   N   P   K   V   V   I   M   L   125

GGT ACC AAT AAC ACC TAT TTC AAC AGC GCG GAA CAA ATC GCG GAA GGA TTG  426
 G   T   N   N   T   Y   F   N   S   A   E   Q   I   A   E   G   L   142

AAG CTG CTG GTG GCC GAA TAC CAG AAA CGC TGT CCG CAG GCA CAC ATC ATC  477
 K   L   L   V   A   E   Y   Q   K   R   C   P   Q   A   H   I   I   159

CTG ATG GGT GTT TTC CCG CGC GGC AAG GAC GCT AAC GAT GGC GGT CGC AAG  528
 L   M   G   V   F   P   R   G   K   D   A   N   D   G   G   R   K   176

AAG GTT GCG GAA ATC AAT AAA ATC ATC TCC CGC TAC GCC GAC GGC GAC AAG  579
 K   V   A   E   I   N   K   I   I   S   R   Y   A   D   G   D   K   193
```

Fig. 12B

```
GTA TCG TTC GTG GAC ATC AGC GAC AAG ATG ATC CAG CCC GAC GGC ACC ATC  630
 V   S   F   V   D   I   S   D   K   M   I   Q   P   D   G   T   I   210

TCG ACC GAC ATG ATG CCG GAT TTT GTC CAT CCG ACC GCC AAA GGC TAC GAG  681
 S   T   D   M   M   P   D   F   V   H   P   T   A   K   G   Y   E   227

ATT TGG GGA GAC GCA ATC CTG CCG ATC AAC AAC AAA TAC GCG TGG CCG AAA AAA  732
 I   W   G   D   A   I   L   P   I   N   N   K   Y   A   W   P   K   K   244

TAA TGC GTT ACT GCC CGC GGT AAT TTT TCG GGC TGG TGC CCA TGG TTT TCT  783

TGA ATG CCT TGG AAA ACG CGA ACT GGG TCG AGT ACC GCA  822
```

Fig. 12C

```
native    MNKLHLVISVQLLAVAGSLLAAETIYQDPVPAGANRAAVAVPRNDWYRDVQNKFD-KYSGKPADIVFEGDS  70
rat β                                           MSQGDSNPAAIPHAAEDIQGDDRWMSQHNRFVLDCKDKEPDVLFVGDS  48
human β                                         MSQGDSNPAAIPHAAEDIQGDDRWMSQHNRFVLDCKDKEPDVLFVGDS  48
mouse β                                         MSQGDSNPAAIPHAAEDIQGDDRWMSQHNRFVLDCKDKEPDVLFVGDS  48
human γ                                          MSGEENPASKPTPVQDVQGDGRWMSLHHRFVADSKDKEPEVVFIGDS  47
bovine γ                                         MSDENPASKPTPVQDVQGDGRWMSLHHRFVADSKDKEPEVVFIGDS  47
mouse γ                                         MSGEGENPASKPTPVQDVQGDGRWMSLHHRFVADSKDKEPEVVFIGDS  48
rat γ                                           MSGEGENPASKPTPVQDVQGDGRWMSLHHRFVADSKDKEPEVVFIGDS  48 native    ITNRWEGTGKAVWKEHFEG-RAADFGIEGDRVENALWRLSKGQVDDINPKVVVIMLGTNNTYFNSAEQI  138
rat β     MVQLMQQY--EIWRELFSPLHALNFGIGGDTTRHVLWRLKNGELENIKPKVIVVWGTNN-HENTAEEV  114
human β   MVQLMQQY--EIWRELFSPLHALNFGIGGDTTRHVLWRLKNGELENIKPKVIVVWGTNN-HENTAEEV  114
mouse β   MVQLMQQY--EIWRELFSPLHALNFGIGGDTTRHVLWRLKNGELENIKPKVIVVWGTNN-HENTAEEV  114
human γ   LVQLMHQC--EIWRELFSPLHALNFGIGGDTQHVLWRLENGELEHIRPKIVVVWGTNN-HGHTAEQV  113
bovine γ  LVQLMHQC--EIWRELFSPLHALNFGIGGDTQHVLWRLENGELEHIRPKIVVVWGTNN-HGHTAEQV  113
mouse γ   LVQLMHQC--EIWRELFSPLHALNFGIGGDSTQHVLWRLENGELEHIRPKIVVVWGTNN-HSHTAEQV  114
rat γ     LVQLMHQC--EIWRELFSPLHALNFGIGGDSTQHVLWRLENGELEHIRPKIVVVWGTNN-HSHTAEQV  114
```

Fig. 13A

```
native    AEGLKLLVAEYQKRCPQAHIILMGVFPRGKDANDGGRKKVAEINKII-S-RYADGDKVSFVDISDKMIQ  205
rat β     AGGIEAIVQLINTRQPQAKIIVLGLLPRGEKPNP-LRQKNAKVNQLL-KVSLPKLANVQLLDIDGGFVH  179
human β   AGGIEAIVQLINTRQPQAKIIVLGLLPRGEKPNP-LRQKNAKVNQLL-KVSLPKLANVQLLDTDGGFVH  179
mouse β   AGGIEAIVQLINTRHAQAKIIVLGLLPRGEKPNP-LRQKNAKVNQLL-KVSLPKLANVQLLDIDGGFVH  179
human γ   TGGIKAIVQLVNERQPQARVVVLGLLPRGQHPNP-LREKNRQVNELVRA-ALAGHPRAHFLDADPGFVH  178
bovine γ  TGGIKAIVQLVNERQPQARVVVLGLLPRGQHPNP-LREKNRRVNELVRA-ALAGHPRAHFLDADPGFVH  178
mouse γ   TGGIKAIVQLVNKLQPQARVVVLGLLPRGQHPNP-LREKNRQVNELVRA-ALAGYPRAHFLDADPGFVH  179
rat γ     TGGIKAIVQLVNKLQPQARVVVLGLLPRGQHPNP-LREKNRQVNELVRA-ALAGYPRAHFLDADPGFVH  179 native    PDGTISTDMMPDFVHPTAKGYEIWGDAILPINNKYAPKK.                              244  (SEQ ID No. 31)
rat β     SDGAISCHDMFDFLHLTGGGYAKICKPLHELIMQLLEETPEEKQTTIA                      229  (SEQ ID No. 32)
human β   SDGAISCHDMFDFLHLTGGGYAKICKPLHELIMQLLEETPEEKQTTIA                      229  (SEQ ID No. 33)
mouse β   SDGAISCHDMFDFLHLTGGGYAKICKPLHELIMQLLEETPEEKQTTIA                      229  (SEQ ID No. 34)
human γ   SDGTISHHDMYDYLHLSRLGYTPVCRALHSLLLRLLAQDGQGAPLLEPAP                    231  (SEQ ID No. 35)
bovine γ  SDGTISHHDMYDYLHLSRLGYTPVCRALHSLLLRLLTQDGQGGAPLPEPSP                   232  (SEQ ID No. 36)
mouse γ   SDGTISHHDMYDYLHLSRLGYTPVCRALHSLLLRLLRLLAQDGQGGIPLPETAS                232  (SEQ ID No. 37)
rat γ     SDGTISHHDMYDYLHLSRLGYTPVCRALHSLLLRLLAQDGQGGIPLPETAP                   232  (SEQ ID No. 38)
```

Fig. 13B

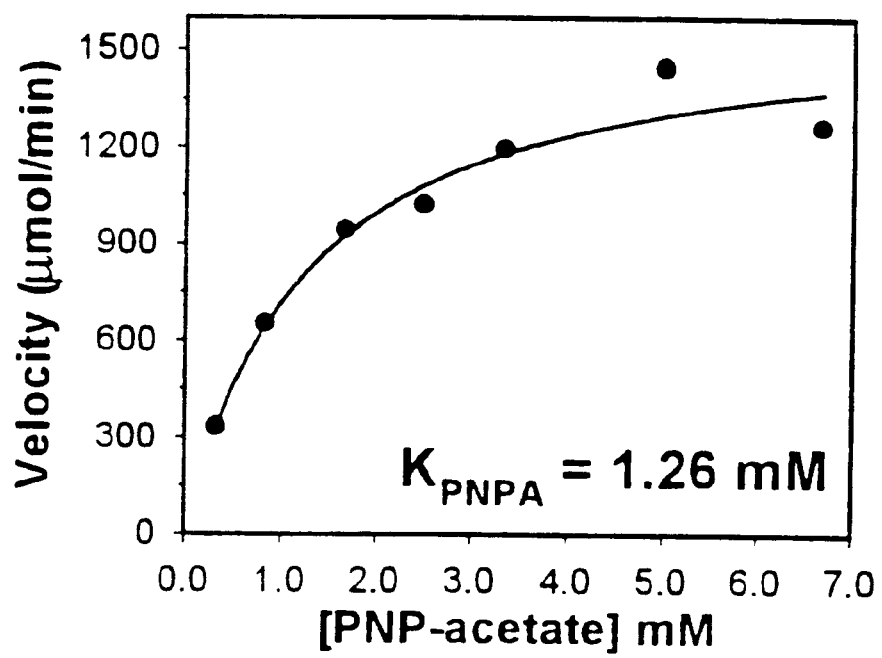
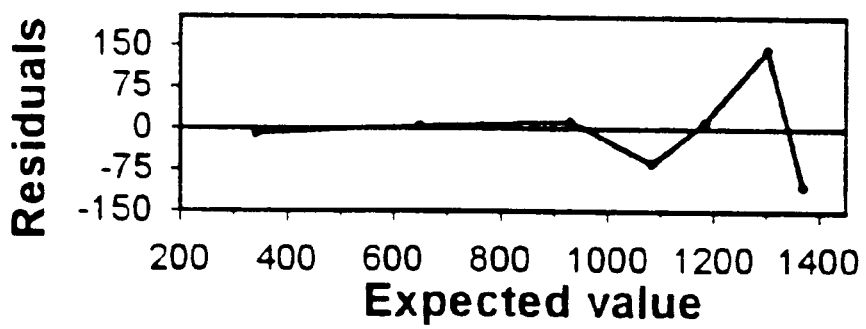
Fig. 19B

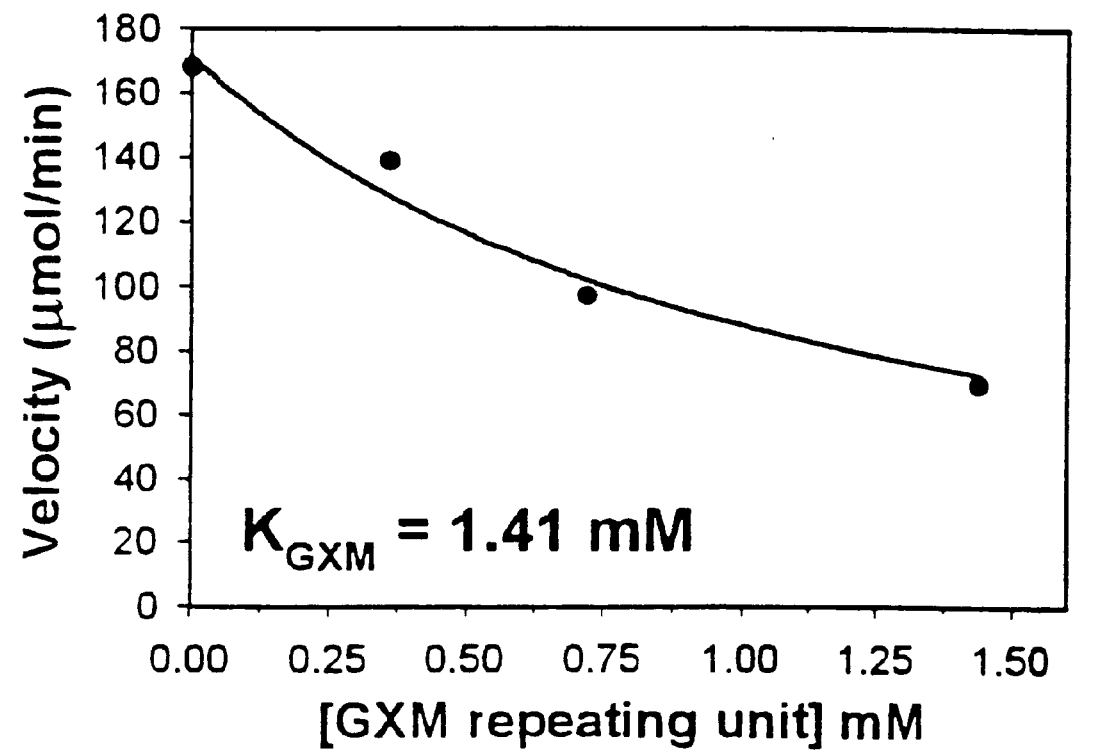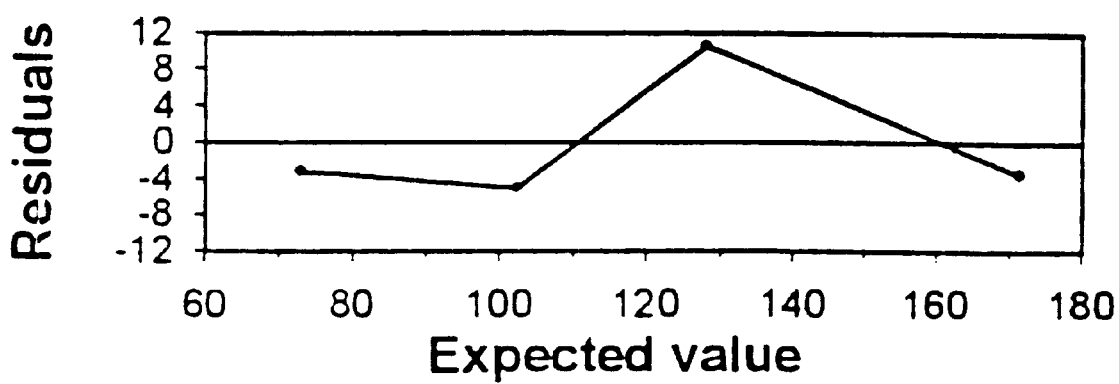
Fig. 20A

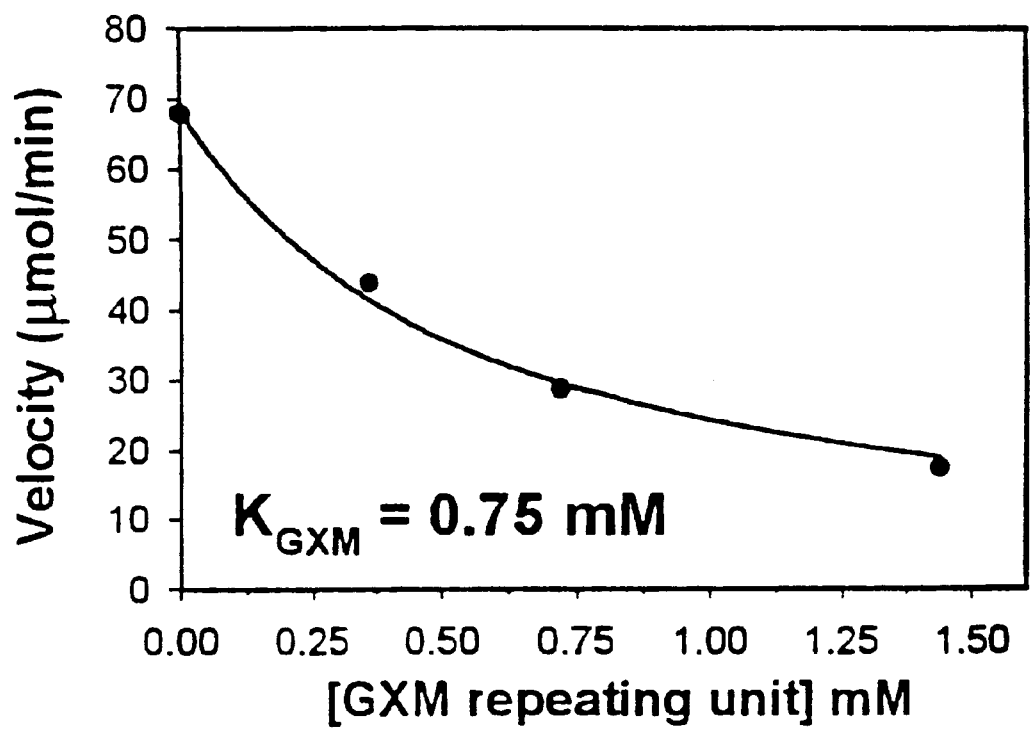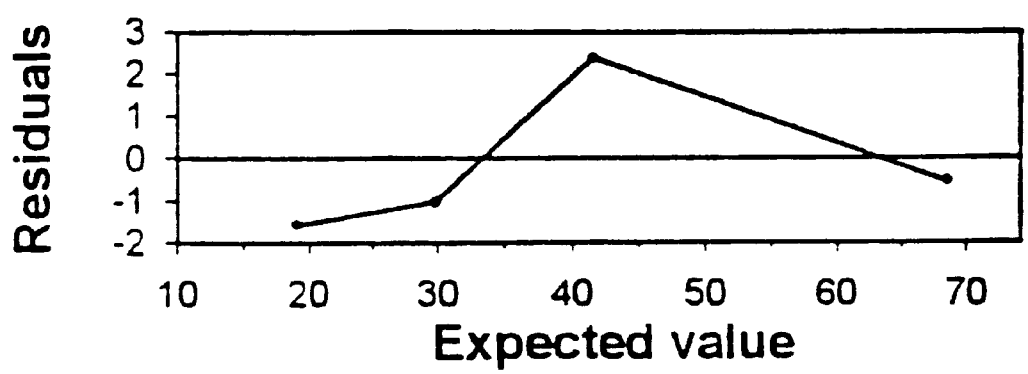
Fig. 20B

GLUCURONOXYLOMANNAN (GXM)-O-ACETYLHYDROLASE OF *CRYPTOCOCCUS NEOFORMANS* AND USES THEREOF

This is a divisional application of U.S. Ser. No. 09/371,710 filed on Aug. 9, 1999 now U.S. Pat. No. 6,146,868.

BACKGROUND OF THE INVENTION

1. Field of the Invention

The present invention relates generally to the fields of molecular biology and molecular structure of *Cryptococcus neoformans*. More specifically, the present invention relates to cloning, sequencing and expression of a gene encoding an enzyme which de-O-acetylates glucuronoxylomannan of *Cryptococcus neoformans*.

2. Description of the Related Art

*Cryptococcus neoformans* is an encapsulated yeast that exists in two varieties. *C. neoformans neoformans* has been isolated from pigeon droppings and is found worldwide in temperate climates whereas *C. neoformans gattii* has been associated with eucalyptus trees and is found in tropical or subtropical regions (13). Both varieties are pathogenic to humans and can produce fatal infections of cryptococcal meningitis (13). The yeast is most commonly pathogenic in immunosuppressed individuals, particularly those with advanced AIDS (8,49). *C. neoformans* has four distinct capsular serotypes, A through D, which are characterized by unique chemical compositions. (33). The serotype used exclusively for this study is serotype A, which comes from *C. neoformans* var. *neoformans*. This serotype is the cause of most cases of cryptococcal meningitis found in AIDS patients (8,49).

*Cryptococcus neoformans* cells have very large capsules (FIG. 1), which are composed of the polysaccharide, glucuronoxylomannan (GXM). Serotype A GXM has an α-1,3-D-mannose backbone with one β-D-glucuronide and two β-D-xyloside sugars per each trimer of mannose (FIG. 2) (14). The backbone is also O-acetylated, ranging from approximately 3–16.5%(33). It has been shown that the O-acetylation forms part of the antigenic epitope for some monoclonal antibodies (MAbs) (46). These monoclonal antibodies can, therefore, be used for determining the presence and degree of O-acetylation on glucuronoxylomannan through ELISA antibody capture assays.

The capsule has been determined to be the single most important virulence factor for the pathogenicity of *C. neoformans* (33). Acapsular mutant strains produced by several laboratories have been found to be avirulent (12,16,35,38). Glucuronoxylomannan has been shown to affect host resistance in a number of ways including, but not limited to inhibition of phagocytosis (10,11,37), suppression of lymphocyte responses and proliferation (9,43), induction of T-cell dependent and independent immunologic tolerance (36,44,53), and even enhancement of HIV-1 infectivity in vivo (47). Treatment consists of the antimycotic agents, amphotericin B and flucytosine, or the azoles, ketoconazole and fluconazole (45). These treatments are often complicated by existing infections and their treatments as well as having some very severe side effects. The disease presents challenges on many fronts to the medical community.

Another challenge is the high viscosity caused by circulating glucuronoxylomannan, and perhaps encapsulated yeast cells, which are thought by some to lead to cerebral edema (23– 27,39,40). The edema is characterized by increased intracranial pressure and has not been uniformly amenable to surgical intervention. It can evolve rapidly and be fatal. The soluble glucuronoxylomannan also presents a problem in that it is not cleared from the circulation and tissues of the host very efficiently (32a, 32b. 32c and 32d).

Prior to the advent of antibiotic and antimycotic agents, investigators experimented with enzymes that could degrade capsular polysaccharides. The first study of this type involved the use of a bacterium to degrade the polysaccharide capsule of Type III *Streptococcus pneumoniae* (4,15). The bacterium was isolated from a cranberry bog in New Jersey. Several studies followed and were expanded into in vivo studies with mice and rabbits. Enzymes were found to be effective in protection against lethal injections as well as in a curative manner when infections had been firmly established prior to treatment (5,51,52). A glucuronoxylomannan-hydrolase was discovered in a similar manner by Gadebusch in 1960. Soil samples tested for enzymatic activity led to isolation of a Gram-negative rod, designated Alcaligenes sp. S-3723, which completely degraded the capsule of *C. neoformans* (17–20). At the time of the Gadebusch report, the composition and structure of GXM was incompletely and sometimes erroneously understood. In retrospect, the Gadebusch was probably a mixture of two or more unidentified and uncharacterized enzymes. The enzyme cocktail was tested in vivo on mice infected with *C. neoformans*. The $ET_{50}$ increased from 18 days for mice with no treatment to 47 days for enzyme-treated mice.

Gadebusch's findings on this enzyme were published in 1960 and 1961 (17–20). Amphotericin B was gaining acceptance as a lifesaving treatment for cryptococcal meningitis and the disease was not very prevalent at that time. Molecular cloning had yet not been conceived, making the use of enzymic treatments tedious and costly, as enzyme had to be purified through a lengthy process from native bacteria. Today, *C. neoformans* infects 5–10% of AIDS patients in the U.S. and is the most common life threatening opportunistic fungal infection in AIDS (34). Antimycotic treatments prolong survival of these patients, but are ineffective against the cerebral edema and have little impact on high serum titers of antigen. Enzyme treatment may be the answer to this lingering problem.

The prior art is deficient in the lack of identification of specific GXM-cleaving enzymes and the lack of a gene encoding an enzyme that modifies the structure of the capsular polysaccharide of *C. neoformans*. Further, the prior art is deficient in the lack of means to block the deleterious activities of GXM that occur during the course of cryptococcosis. The present invention fulfills this long-standing need and desire in the art.

SUMMARY OF THE INVENTION

The present invention discloses the cloning, sequencing, expression, and characterization of a novel enzyme shown to de-O-acetylate glucuronoxylomannan. This novel enzyme was isolated from a mixture of microorganisms that were cultured from a sample of sewage sludge obtained from the Washoe County sewage treatment plant. The microbial culture produced a group of enzymes that fully degrade glucuronoxylomannan. The culture contains an unknown number of microbial species which have, as yet, not been identified. The culture does not grow well, if at all, when the species are separated, making identification of the different culture components difficult. The enzymatic activity appears to be the result of a minimum of four enzymes: mannosidase, xylosidase, glucuronidase. and O-acetylhydrolase (FIG. 2). The O-acetylhydrolase was the first of the group to be purified. Following purification, the GXM-O-acetylhydrolase was subjected to peptide mapping which provided six partial amino acid sequences (Table 1): These fragments define the starting point for the cloning of a gene that encodes the enzyme.

TABLE 1

Sequences from Peptide Mapping of Purified Native GXM-O-Acetylhydrolase and Its LysC-Cleaved Fragments

| Peptide | N-Terminal Amino Acid Sequences |
| --- | --- |
| Whole protein | AETIYQDPVPAGANRAAVAVPRNDWYRD VQNKFDKYSGKPADIVF (SEQ ID No. 1) |
| LysC-cleaved fragments | |
| peptide 1* | YSGKPADIVFEGDSITNR (SEQ ID No. 2) |
| peptide 2 | MIQPDGTISTDMMPDFVIIPT (SEQ ID No. 3) |
| peptide 3 | IISRYADGDFVSFVDII (SEQ ID No. 4) |
| peptide 4 | EHFEGRAADFGIEGDRVENAL (SEQ ID No. 5) |
| peptide 5 | GYEIWGDAILPINN (SEQ ID No. 6) |

*This sequence is a continuation of the whole protein N-terminal sequence.

The present invention is directed to DNA encoding glucuronoxylomannan (GXM)-O-acetylhydrolase, wherein the DNA is selected from the group consisting of (a) isolated DNA which encodes GXM-O-acetylhydrolase; (b) isolated DNA which hybridizes to isolated DNA of (a) and which encodes GXM-O-acetylhydrolase; and (c) isolated DNA differing from the isolated DNAs of (a) and (b) in codon sequence due to the degeneracy of the genetic code, and which encodes GXM-O-acetylhydrolase. Preferably, the DNA has the sequence shown in SEQ ID No. 30 and the enzyme GXM-O-acetylhydrolase has the amino acid sequence shown in SEQ ID No. 31.

The present invention also provides a vector capable of expressing the above DNA and a host cell transfected with the vector.

The present invention is also directed to degenerate primers used for PCR screening for the DNA disclosed herein and primers used for cloning the DNA into an expression vector.

The present invention is further directed to isolated and purified GXM-O-acetylhydrolase coded for by DNA selected from the group consisting of (a) isolated DNA which encodes GXM-O-acetylhydrolase; (b) isolated DNA which hybridizes to isolated DNA of (a) and which encodes GXM-O-acetylhydrolase; and (c) isolated DNA differing from the isolated DNAs of (a) and (b) in codon sequence due to the degeneracy of the genetic code, and which encodes GXM-O-acetylhydrolase. Preferably, the isolated and purified GXM-O-acetylhydrolase has the amino acid sequence shown in SEQ ID No. 31. Also provided is a method of producing the recombinant GXM-O-acetylhydrolase.

The present invention further provides a recombinant GXM-O-acetylhydrolase having an amino acid sequence shown in SEQ ID No. 31.

Still further provided in the present invention is a method of treating cryptococcosis in an individual in need of such treatment by administering GXM-degrading enzymes to the individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows electron micrograph of *Cryptococcus neoformans.*

FIG. 2 shows structure of glucuronoxylomannan, serotype A.

FIGS. 3A and 3B show pGEM T-Easy vector map.

FIGS. 4A and 4B show pET 28a(+) plasmid map.

FIG. 5 shows the structure of para-nitrophenol synthetic substrates.

FIGS. 6A and 6B show PCR screening strategy.

FIGS. 7A–7D show optimization of PCR.

FIG. 8 shows agarose gel electrophoresis of samples to be sequenced.

FIG. 9 shows contiguous alignment of PCR product sequences and initial nucleotide sequence of the GXM-de-O-acetylhydrolase gene. FIG. 9A shows forward and backward sequencing reactions. FIG. 9B shows the nucleotide (SEQ ID No. 28) and deduced amino acid sequences (SEQ ID No. 29) from the contiguous alignment. The amino acid sequences obtained by peptide mapping are underlined. The PCR primers used for the initial screening are underlined by solid arrows.

FIG. 10 shows Southern blot of complete restriction enzyme digestion of genomic DNA.

FIG. 11 shows agarose gel electrophoresis of inverse PCR products.

FIGS. 12A–12C show full nucleotide sequence and deduced amino acid sequence of the GXM O-acetylhydrolase.

FIGS. 13A and 13B show alignment of deduced amino acid sequence with BLAST homology search results.

FIGS. 19A and 19B show Michaelis and Menton plot of varied [PNPA] with constant [E].

FIGS. 20A and 20B show effect of GXM on PNPA hydrolysis.

DETAILED DESCRIPTION OF THE INVENTION

Figure 1:
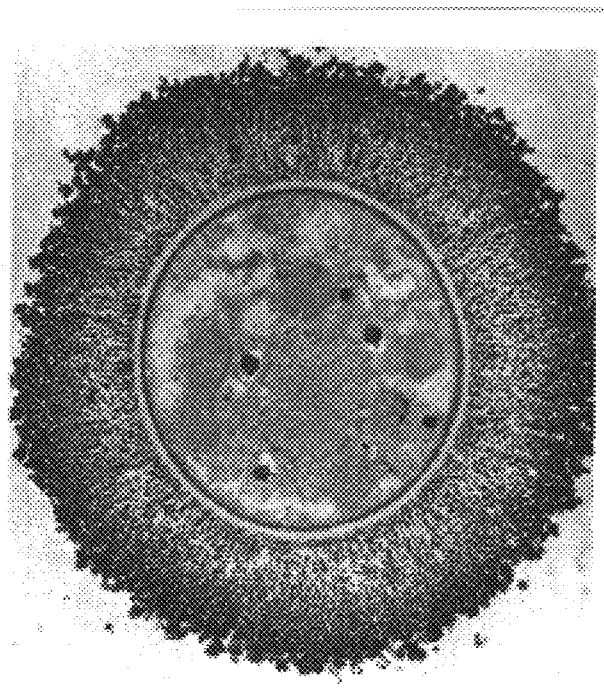
Figure 2:
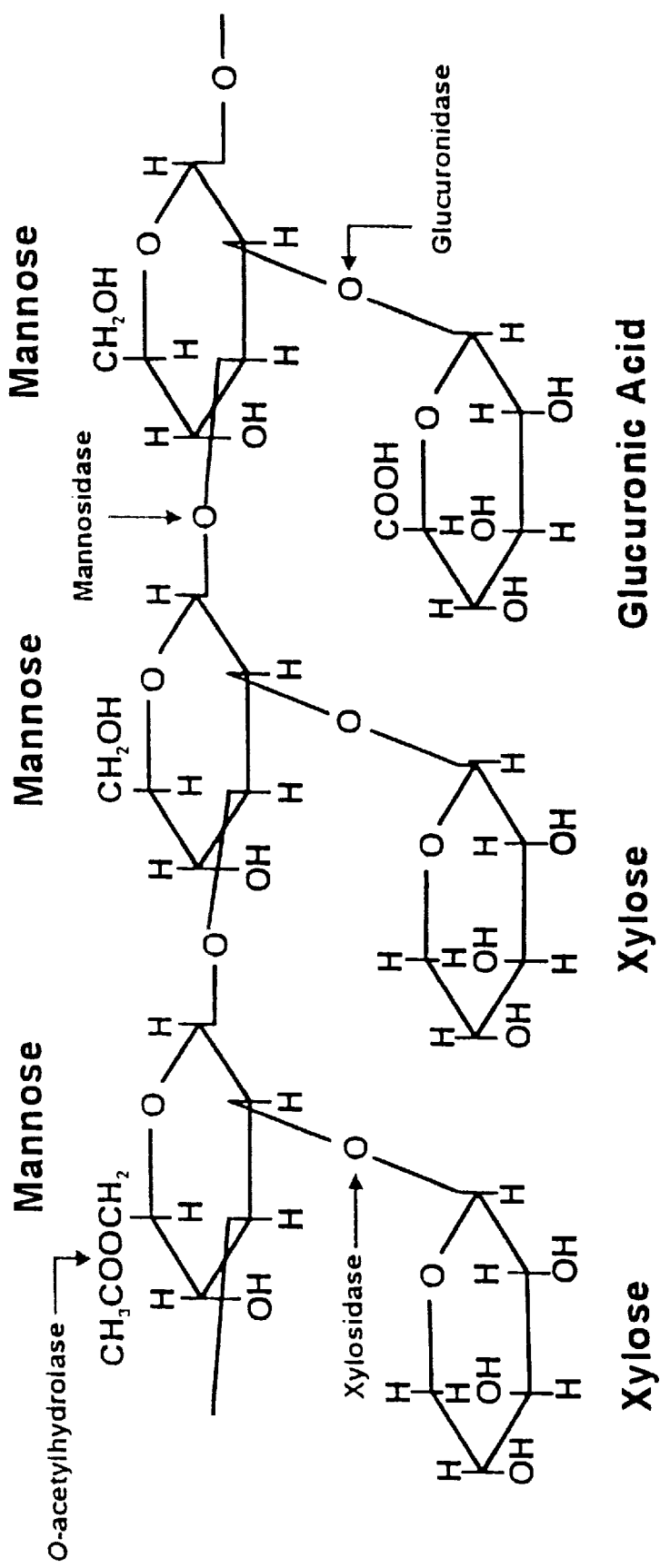

An essential virulence factor of *Cryptococcus neoformans* is its capsular polysaccharide, whose primary constituent is glucuronoxylomannan. Glucuronoxylomannan not only contributes to the production of disease, but is also thought to contribute to high intracranial pressure found, in some patients. This high intracranial pressure may be due to the high viscosity of glucuronoxylomannan that has been shed during infection. Early studies by Gadebush have shown that mice infected with *Cryptococcus neoformans* were saved by treatment with a GXM-degrading enzyme. Given the number of glucosidic bonds contained in GXM, it is most likely that the Gadebusch preparation was a crude mixture of enzymes.

The present invention is directed to the cloning, sequencing, and expression of a glucuronoxylomannan-degrading enzyme. PCR techniques were used to screen the wild-type genomic DNA with primers designed from peptide sequence obtained from the native enzyme. The recombinant protein was expressed in a pET plasmid system and purified through metal chelate chromatography. The recombinant and native have been shown to have the same substrate specificity and similar $K_m$ values for those substrates.

In one embodiment of the present invention, there is provided DNA encoding glucuronoxylomannan (GXM)-O-acetylhydrolase, wherein the DNA is selected from the group consisting of (a) isolated DNA which encodes GXM-O-acetylhydrolase; (b) isolated DNA which hybridizes to isolated DNA of (a) and which encodes GXM-O-acetylhydrolase; and (c) isolated DNA differing from the isolated DNAs of (a) and (b) in codon sequence due to the degeneracy of the genetic code, and which encodes GXM-O-acetylhydrolase. Preferably, the DNA has the sequence shown in SEQ ID No. 30 and the enzyme GXM-O-acetylhydrolase has the amino acid sequence shown in SEQ ID No. 31.

In another embodiment of the present invention, there are provided a vector capable of expressing the above DNA adapted for expression in a recombinant cell and regulatory elements necessary for expression of the DNA in the cell.

In still another embodiment of the present invention, there is provided a host cell transfected with the above vector, which expresses GXM-O-acetylhydrolase. Preferably, the host cell is selected from group consisting of bacterial cells, mammalian cells, plant cells and insect cells. More preferably, the bacterial cell is *E. coli*.

The present invention is also directed to a degenerate N-terminal primer used for PCR screening for the DNA disclosed herein in a culture, wherein the primer is selected from the group consisting of SEQ ID Nos. 7 and 9; a degenerate reverse internal primer used for PCR screening, wherein the primer is selected from the group consisting of SEQ ID Nos. 12, 15, 18 and 21; and a degenerate primer used for inverse PCR to obtain the start and stop codons of the DNA, wherein the primer is selected from the group consisting of SEQ ID Nos. 24 and 26. Further provided is a primer used for cloning the DNA into an expression vector, wherein the primer is selected from the group consisting of SEQ ID Nos. 40 and 47.

The present invention also provides isolated and purified glucuronoxylomannan-O-acetylhydrolase coded for by DNA selected from the group consisting of (a) isolated DNA which encodes GXM-O-acetylhydrolase; (b) isolated DNA which hybridizes to isolated DNA of (a) and which encodes glucuronoxylomannan-O-acetylhydrolase; and (c) isolated DNA differing from the isolated DNAs of (a) and (b) in codon sequence due to the degeneracy of the genetic code, and which encodes GXM-O-acetylhydrolase. Preferably, the isolated and purified GXM-O-acetylhydrolase has the amino acid sequence shown in SEQ ID No. 31.

In still yet another embodiment of the present invention, there is provided a recombinant GXM-O-acetylhydrolase having an amino acid sequence shown in SEQ ID No. 31, wherein the recombinant GXM-O-acetylhydrolase is encoded by a nucleic acid segment comprising a sequence shown in SEQ ID No. 30.

In still yet another embodiment of the present invention, there is provided a method of producing the recombinant GXM-O-acetylhydrolase, comprising the steps of obtaining a vector that comprises an expression region comprising a sequence encoding the amino acid sequence shown in SEQ ID No. 31 operatively linked to a promoter; transfecting the vector into a cell; and culturing the cell under conditions effective for expression of the expression region.

The present invention is further directed to a method of treating cryptococcosis in an individual in need of such treatment by administering the enzymes, alone or in combination with additional GXM hydrolases to the individual. Preferably, the individual suffers from one or more complications of cryptococcal meningitis, particularly cerebral edema. Further provided is a kit containing purified glucuronoxylomannan-O-acetylhydrolase.

The following examples are given for the purpose of illustrating various embodiments of the invention and are not meant to limit the present invention in any fashion.

EXAMPLE 1

Cloning and Sequencing

Purification, LysC Degradation and Amino Acid Sequencing of Wild-Type Enzyme:

The native GXM O-acetylhydrolase was purified from a mixed unknown bacterial culture that was collected from sewage. The purification was achieved by the following steps: cholate extraction, ammonium sulfate precipitation, molecular sieve chromatography, and ion exchange on a mono Q column followed by a mono S column.

Amino acid sequencing of the native protein was conducted by K Schegg of the Core Protein Facility of the University of Nevada using Edman degradation on a Procise 492 sequencer (Applied Biosystems). After the NH$_2$-terminal sequence was determined, the protein was subjected to LysC endoproteinase degradation, and the fragments were separated on a Microhm UMA HPLC under the following conditions: column-Reliasil C18, 5 µm, 300 Å; guard column—silica based C18; solvent A—0.1% TFA;

solvent B—0.09% TFA, 60% acetonitrile; wash solvent—20% methanol, 80% diH$_2$O; temperature 40° C.; gradient 1–100% solvent B over 60 minutes.

DNA Preparation:

Genomic DNA was isolated from the mixed bacterial culture using Puregene Cell Lysis Solution and Protein Precipitation Solution (Gentra Systems) according to the manufacture's instructions. Agarose gel electrophoresis was performed according to Sambrook et. al. (50). DNA was extracted from agarose gels using the Qiax II Agarose Gel Extraction kit (Qiagen) according to manufacturer's instructions. Restriction enzymes and T4 DNA ligase were purchased from Promega and New England Biolabs and used with buffers provided by the suppliers.

Bacterial Strains, Culture Conditions, Plasmids and Oligonucleotides:

Wild-type bacterial culture, a mixed culture of unknown organisms which was obtained from a sewage culture, was maintained in a glycerol stock at −20° C. The culture was grown in a shaking 30° C. incubator on 1× YNB/MES/GXM media at a pH of 6.0: yeast nitrogen base (6.7 g/l), 20 mM MES buffer, and GXM (400 mg/l).

E. coli Max Efficiency DH5α (Gibco BRL, Life Technologies) and JM109 High Efficiency Competent Cells (Promega) were used as hosts for recombinant plasmids. The E. coli transformants were grown at 37° C. on LB (Luria-Bertani broth) medium with ampicillin a t a final concentration of 100 µg/ml, X-Gal (5-bromo-4-chloro-3-indolyl β-D-galacto-pyranoside) at a final concentration of 80 µg/ml and IPTG (isopropyl β-D-Thiogalactopyranoside) at a final concentration of 0.5 mM. The transformant colonies were inoculated into 5 ml of LB medium containing ampicillin and grown overnight in a shaking 37° C. incubator.

Figure 3A:
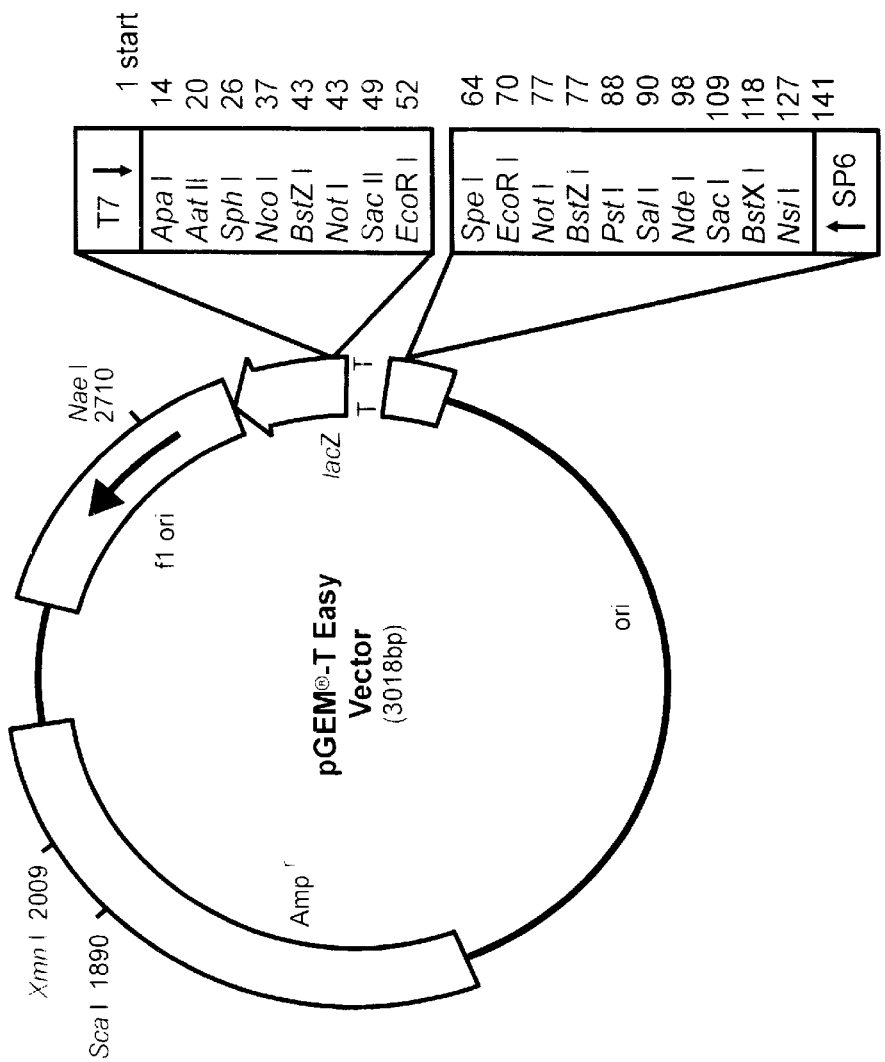
Figure 3B:
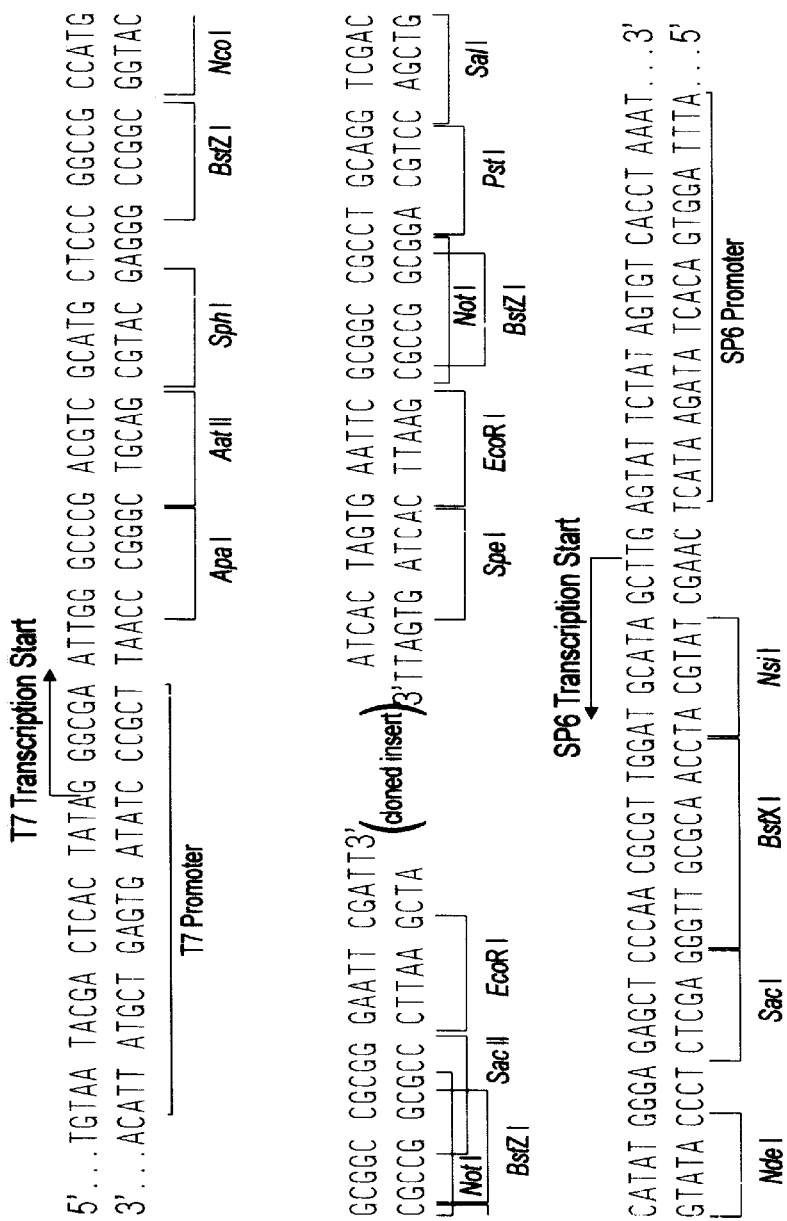

Promega Is pGEM® T-Easy Vector System was used for subcloning PCR fragments and to prepare double stranded DNA for sequencing. These vectors contain T7 and SP6 RNA Polymerase promoters flanking a multiple cloning site found in the β-galactosidase coding region (FIGS. 3A and 3B).

Oligonucleotides were either purchased from Integrated DNA Technologies or Gibco BRL Life Technologies or synthesized by E Otteson of the DNA Analysis Lab of the University of Nevada, Reno, on a PCR-MATE EP 391 DNA Synthesizer (Applied Biosystems) using the phosphoramidite method of oligonucleotide synthesis.

PCR Amplification:

PCR was conducted according to McPherson et. al. (42). PCR amplification mixtures (50 µl for screening and 20 µl for sequencing reactions) contained DNA template (0.3–2 µg), deoxynucleotide triphosphates (10 nmol each), oligonucleotide primers (0.3–1 µg each), and taq DNA polymerase (Promega) (2.5–5 U) in 1.5 mM MgCl$_2$ buffer (Promega). The reactions were carried out on a Gene Amp PCR System 9600 (Perkin Elmer) for 30 cycles, each with one minute denaturation at 95° C., one minute annealing at 50°–63° C. (depending on melting temperature, T$_m$, of primers) and one minute extension at 72° C. The final elongation step was 10 min at 72° C. The Tm was provided with oligonucleotides at time of delivery. The PCR products were separated by gel electrophoresis and then extracted and purified with the Qiax II Agarose Gel Extraction Kit (Qiagen).

Nucleotide Sequencing: Recombinant pGEM7 T-Easy vectors containing PCR products from the initial screening of genomic DNA were isolated from E. coli using QIAprep Spin Miniprep Kit (Qiagen). These plasmids were used as templates in a sequencing PCR reaction with Terminator Ready Reaction Mix from the ABI PRISM Dye Terminator Cycle Sequencing Ready Reaction Kit (Applied Biosystems, Perkin Elmer). This Terminator Ready Reaction Mix labeled the PCR products at the 3' terminal position with a fluorescently labeled dideoxy-nucleotide in preparation for sequencing. The PCR products were sequenced by J. Rowe of the Core Sequencing Facility of the University of Nevada, Reno using the dideoxy-nucleotide chain termination method on an ABI PRISM 310 Genetic Analyzer (Applied Biosystems).

Southern Blot Analysis:

Genomic DNA was isolated, digested with EcoRI, Hae III, and Hind III (Promega) and separated by agarose gel electrophotesis. After electrophoresis, the gel was soaked in 0.4 M NaOH, 0.6 M NaCl for 30 minutes at room temperature. The DNA was transferred from the gel to a Biodyne® B Membrane (Gibco BRL) that had been soaked for 15 minutes in 0.4 M NaOH. The transfer took place in a BIOS Blotting Unit. Following blotting, the membrane was washed in 0.2 M Tris-HCl (pH 7.5), 2×SSC (0.9 M NaCl, 0.09 M sodium citrate, pH 7.0) for 15 minutes with gentle shaking at room temperature. The membrane was dried in an 80° C. oven for 60 minutes.

Oligonucleotide probes (~10 µmol) were radiolabled with [γ-$^{32}$]ATP (150 µCi) (DuPont) and T4 Polynucleotide Kinase (8–10 U) (Promega). After overnight incubation at room temperature, free radio-label was removed from the mixture using the Stratagene Push Column Beta Shield Device and NucTrap® Probe Purification Columns. The labeled probes were quantitated on a Beckman LS 3801 Scintillation Counter.

Dried membranes were hybridized with radiolabeled probes in a hybridization solution of 1.5×SSPE (3.0 M NaCl, 0.2 M NaH$_2$PO$_4$, 0.02 M EDTA, pH 7.4), 7% SDS, 10% PEG 8,000, and diH$_2$O. The hybridization mixture consisted of 10 ml hybridization solution, one ml salmon sperm DNA (10 mg/ml) (Gibco-BRL), and 12 µl radiolabeled probe. This was rotated in a glass tube with the membrane overnight at 65° C.

Hybridized membrane was washed 30 minutes at room temperature with gentle shaking in 2×SSC, 0.1% SDS and then 30 minutes at 55° C. with gentle shaking in 0.1×SSC, 0.1% SDS. The membrane was blotted dry, wrapped in plastic wrap and placed in a cartridge with X-ray film at −80° C. for 6 hours initial exposure. The film was developed on a Konica Medical Film Processor QX-70. Membranes were stripped by washing for one hour at 55° C. in 0.4 M NaOH and then neutralized by washing 30 minutes in 0.2 M Tris-HCl (pH 7.5), 2×SSC. Hybridization was then repeated as needed.

EXAMPLE 2

Homology Search

A computer search was conducted through the National Center for Biotechnology Information (NCBI) Basic Local Alignment Search Tool (BLAST) search engine with the amino acid sequence. This is a search algorithm largely based on the statistical methods of Karlin and Altschul (30,31). The program compares an amino acid query sequence against a number of sequence data bases and scores that comparison based on the statistical significance of similarity in their sequences. Results are provided in the form of an overall score, an E value, an identities score, and a positives score. The score is unique to the residue composition for the query and database sequences and to the total length of the query sequence and the database. This raw alignment score is followed by an alternate dimension of bits, which is independent of the scale to which the score is calculated and can provide some cross-sequence comparisons. A higher bits score indicates a higher degree of sequence similarity. The E value (Expect value) is related to a P value (Probability value) and relates the expected number of hits when searching a database of a particular size. The identities score relates the number and fraction of identical residues between query and database. This number is often referred to as the degree of homology. The positives score relates the number and fraction of residues for which the alignment scores have a positive value.

Another search was conducted through the PSORT search engine, also with the amino acid sequence. PSORT predicts the presence of signal sequences by McGeoch's method (41) modified by Nakai and Kanehisa (42), and scores the sequence using three parameters: the net charge of the N-terminal region, the length of the central hydrophobic region, and the peak value of the central hydrophobic region. A large positive score indicates a high possibility that the protein possesses a signal sequence.

PSORT also applies another method of signal recognition developed by von Heijne (54). This method determines the highest probable signal cleavage site based on a weight-matrix method which incorporates information on consensus patterns around the cleavage site. A large positive score indicates a high probability the protein has a cleavable signal sequence. The position of a possible cleavage site is also given in this section of the report.

The lipoprotein nature of the submitted sequence is analyzed using a method developed by von Heijne (55) which incorporates. Mc Geoch's method with von Heijne's method of analyzing consensus sequences surrounding the cleavage site. The result of this test was then submitted to a protocol developed by Yamaguchi et al. (58) which segregates the protein to either the inner or outer membrane.

EXAMPLE 3

Protein Expression

Bacterial Strains, Plasmids, Oligonucleotides and Culture Conditions:

Wild-type bacterial culture, the original mixed culture of unknown organisms which produced the native enzyme, was maintained in a glycerol stock at −20° C. The culture was grown in a shaking 30° C. incubator on 1× YNB/MESIGXM media at a pH of 6.0.

Figure 4A:
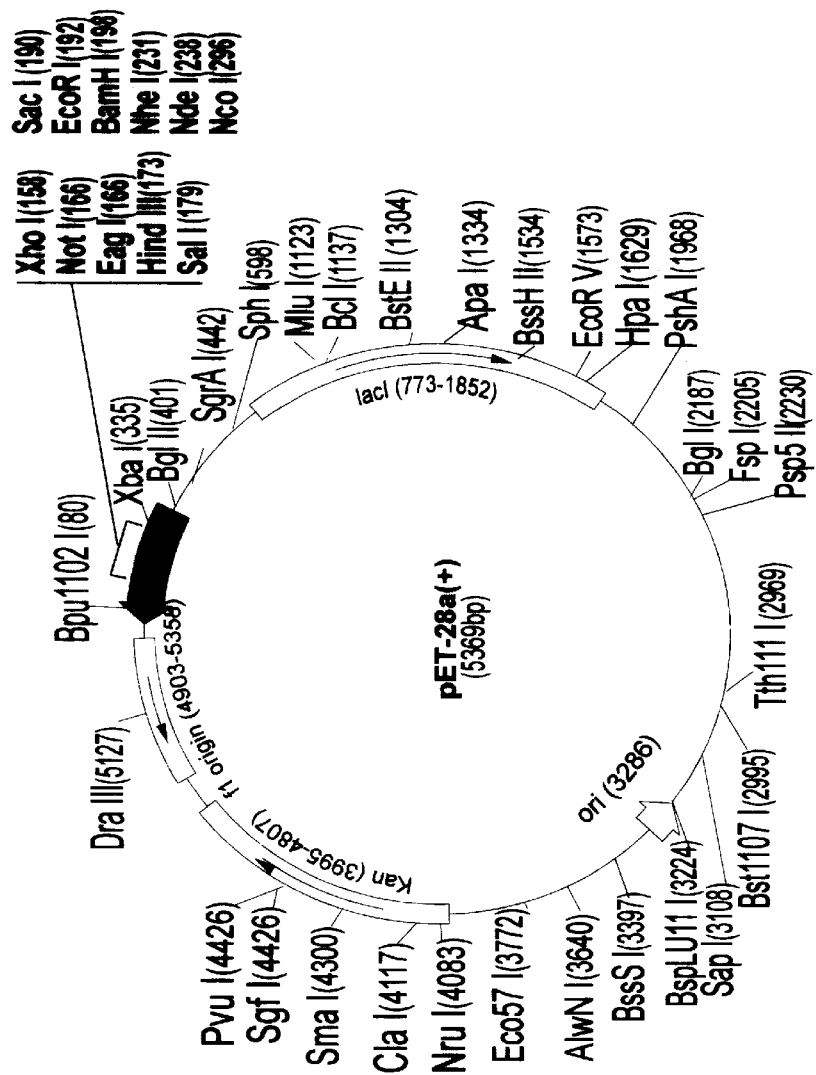
Figure 4B:
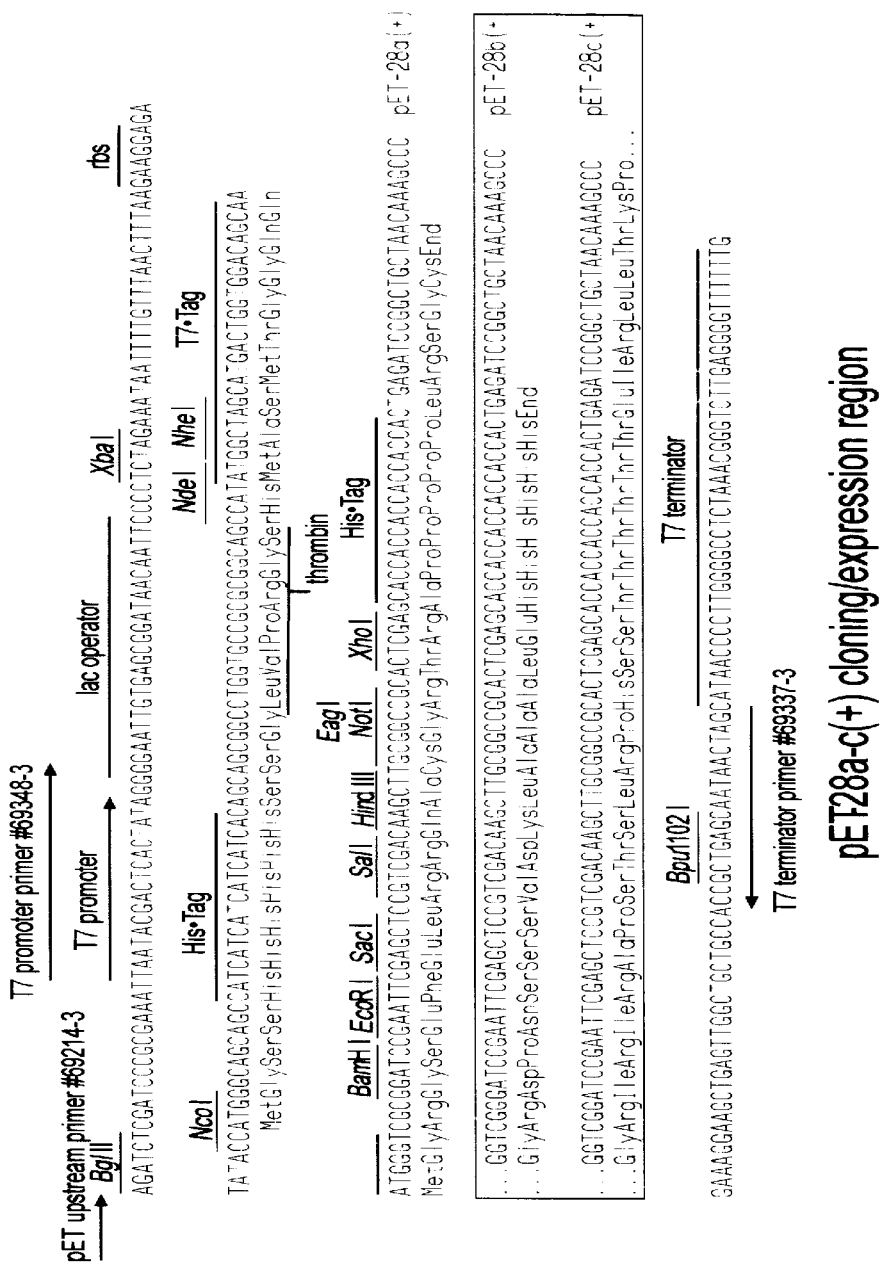
Figure 5:
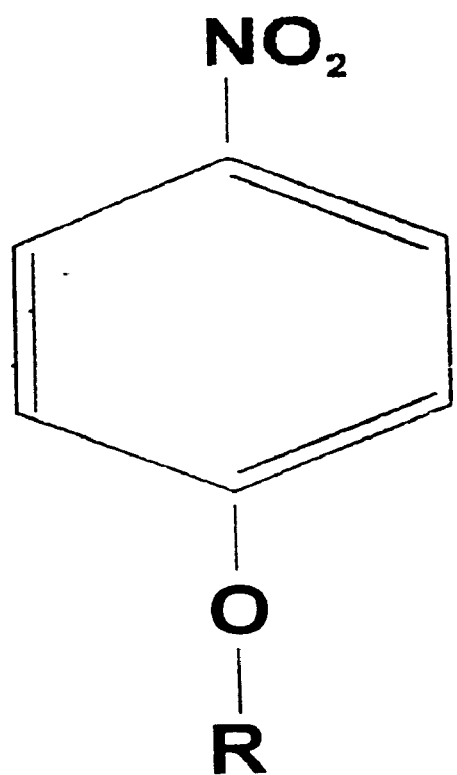

*E. coli* Max Efficiency DH5α (Gibco BRL, Life Technologies), NovaBlue competent cells (Novagen) and BL21(DE3) competent cells (Novagen) were used as hosts for recombinant plasmids. The *E. coli* Max Efficiency DH5α transformants were grown at 37° C. on LB media with ampicillin at a final concentration of 100 μg/ml, X-Gal at a final concentration of 80 μg/ml and IPTG at a final concentration of 0.5 mM. The transformed colonies were inoculated into 5 ml of LB medium containing ampicillin and grown overnight in a shaking 37° C. incubator. The NovaBlue and BL21(DE3) transformants were grown at 37° C. on LB media with kanamycin at a final concentration of 30 μg/ml. pET-28a(+) (Novagen) was used for the expression of recombinant proteins and to confer kanamycin resistance for selection (FIGS. 4A and 4B). The plasmid contains both a C-terminal and an N-terminal 6×HisXtag for purification by nickel-chelation chromatography. Oligonucleotides were synthesized by either Integrated DNA Technologies or Gibco BRL Life Technologies.

PCR Modification of Target Gene for Insertion into pET Plasmid:

PCR amplification mixtures (50 μl) contained DNA template (0.3–2 μg), deoxynucleotide triphosphates (10 nmol each), oligonucleotide primers (0.3–1 μg each), and taq DNA polymerase (Promega) (2.5–5 l) in 1.5 mM MgCl$_2$ buffer (Promega). The reactions were carried out on a PowerBlock System, Easy Cycler Series (ERICOMP, Inc.) for 30 cycles, each with 30 seconds denaturation at 94° C., 30 seconds annealing at 60° C. and one minute extension at 72° C. The final elongation step was 10 minutes at 72° C. The PCR Purification System (Gibco BRL, Life Technologies) was used to purify the products.

Colony PCR:

Colony PCR was used to screen colonies of transfected non-expression host bacteria. Products were separated by gel electrophoresis and then purified with the CONCERT Rapid PCP Two colonies were picked from each plate for use as the template in a colony PCR, these colonies were also freshly plated at that time to ensure continuation of any positive transformant cell lines. Mixtures (50 μl) were set up as described in previous section. They were run on the same system for 35 cycles, each with one minute denaturation at 94° C., one minute anneal at 55° C. and two minutes extension a t 72° C. The final elongation step was six minutes at 72° C. The products of this reaction were separated by agarose gel electrophoresis to determine if the subcloning was successful.

Vector Preparation:

pET28a(+) vector (3 μg) was prepared to receive the insert by restriction digestion with 10–20 μl of both BamHI and NdeI and 10× BamHI buffer (recommended for this double digestion by New England Biolabs) in a total volume of 30 μl with diH$_2$O. The digested vector was separated by agarose gel electrophoresis, excised and purified as previously described. The insert, which consisted of PCR products, was double digested in the same manner.

Transfection of *E. coli* Cells:

Recombinant plasmids were first cloned into non-expression hosts, analyzed to identify positive clones, then transformed into the expression host with T7 RNA polymerase gene. The transfection procedure was the same for each host. Competent cells were thawed, mixed gently and divided into 20 μl aliquots. Each aliquot received 1 μl of recombinant plasmid and was placed on ice for 20 minutes. The samples were heat shocked at 42° C. for 40 seconds and then placed back on ice for two minutes. S.O.C. medium (2% tryptone, 0.5% yeast extract, 10 mM NaCl, 2.5 mM KCl, 10 mM. MgCl$_2$, 10 mM MgSO$_4$, and 20 mM glucose) (80 μl) was added to each reaction before shaking at 200–250 rpm and 37° C. for one hour. Transformation mixture (50 μl) was spread on LB agar plates containing 30 μg/ml kanamycin and incubated overnight a t 37° C.

Induction of λDE3 Lysogens:

Expression of a target gene in an λDE3 lysogen strain of *E. coli* is induced by the addition of IPTG to a growing culture to a final concentration of 1.0 mM. A single colony was picked from the expression host transformants and used to inoculate a 50 ml LB containing 30 μg/ml kanamycin in a 250 ml Erlenmeyer flask. This was incubated with shaking at 37° C. for about 4 hours. at which point the O.D.$_{600}$ reached approximately 0. 8. Samples were removed for an uninduced control. IPTG was added as described above to induce the expression of recombinant protein, and shaking incubation was continued as before for two additional hours. In one experiment, samples were removed every 30 minutes throughout this incubation to follow the time course of induction. The samples were separated by SDS-PAGE and tested for enzymatic activity on PNP-acetate. In another experiment, the full culture was devoted to purification. In this experiment, the flask was cooled on ice for 5 minutes and cells were collected by centrifugation at 5000×g for 5 minutes at 4° C. The cells were resuspended in 0.25 culture volume of cold 50 mM Tris-HCl pH 8.0 at 25° C. and centrifuged again as above. At this point, the cells were either stored in a pellet form at −80° C. or prepared for protein purification.

Purification of His-Tagged Recombinant Enzyme under Non-Denaturing Conditions:

The rapid affinity purification of recombinant proteins was possible because the pET vector carries NB and C-terminal histadine hexapeptides. The His•Bind resin supplied by Novagen for use in the column binds these histidine tags and, therefore, the recombinant protein. Unbound proteins were washed away and the target protein was eluted with imidazole. After elution, the protein was dialyzed into PBS with 0.05% Tween 20, as activity was abolished in the presence of imidazole. Tween 20 reduced the amount of protein adherence to storage containers.

Prior to purifying the protein, crude fractions (soluble, insoluble and media) of the cell lysate were analyzed for enzymatic activity. The medium of a 50 ml culture was collected after centrifugation. Trichloroacetic acid (TCA) (50 $\mu$l) was added to 1.5 ml of the medium to precipitate any proteins present. The mixture was placed on ice for 15 minutes and then subjected to centrifugation to pellet the precipitated proteins. The pellet was washed with acetone, air dried and resuspended in PBS-Tween. This was tested for enzymatic activity using the PNP-acetate assay (para-nitrophenol-assay, description following). The original cell pellet from this 50 ml culture was resuspended in $\frac{1}{10}$ culture volume of 50 mM Tris-HCl pH 8.0. Lysozyme (Sigma) was added to a concentration of 100 $\mu$g/ml, and $\frac{1}{10}$ volume 1% Triton X-100 was added. The mixture was incubated at 30° C. for 15 minutes and then sonicated with a microtip to shear the DNA. The lysate was centrifuged at 12,000×g for 15 minutes at 4° C. The supernatant fluid was tested for soluble enzymatic activity using the same assay as above. The pellet was resuspended in PBS-Tween and tested for insoluble enzyme activity with the same assay.

A 100 ml induced culture was prepared as described in the previous section through the initial centrifugation step following induction and growth. All buffers and the His•Bind resin were degassed under reduced pressure conditions for 20 minutes prior to being used in this procedure. The His•Bind resin (5 ml of a 50% EtOH solution) was loaded and allowed to settle in the column supplied with the pET System (Novagen). The column was washed with sterile diHO (3 volumes), 1× Charge Buffer (5 volumes: 400 mM NiSO$_4$) and 1× Binding Buffer (3 volumes: 40 mM imidazole, 4 M NaCl, 160 mM Tris-HCl, pH 7.9, final pH 7.9) to charge and equilibrate it in preparation for the cellular extract. The cellular extract was pelleted by centrifugation for 5 minutes at 5,000×g. The supernatant fluid was decanted and the pellet was resuspended in ice-cold Binding Buffer (4 ml). The mixture was sonicated briefly to shear chromosomal DNA. The lysate was centrifuged for 10 minutes at 10,000 rpm to remove debris. The supernatant fluid was then filtered through a 0.45 micron membrane to remove any particulates. The supernatant fluid was loaded onto the column. The cell extract was followed with washes of 1× Binding Buffer (10 volumes) and 1× Wash Buffer (6 volumes: 480 mM imidazole, 4 M NaCl, 160 mM Tris-HCl, pH 7.9, final pH 7.9) to wash away any unbound proteins. The bound protein was eluted with 1× Elute Buffer (6 volumes: 4 M imidazole, 2 M NaCl, 80 mM Tris-HCl, pH 7.9, final pH 7.9) followed by 1× Strip Buffer (10 ml: 400 mM EDTA, 2 M NaCl, r80 mM Tris-HCl, pH 7.9, final pH 7.9). Throughout the process, 1.5 ml fractions were collected, starting with the loading of the cellular extract. These were pooled into fractions of 3–9 ml, dialyzed against PBS-Tween, and tested for enzymatic activity.

EXAMPLE 4

Characterization of Recombinant GXM O-acetylhydrolase

Quantitation of Purified Recombinant Enzyme and Approximation of Molecular Mass:

The purified enzyme was quantitated using the BCA method as well as by absorption spectroscopy at 280 nm (a=0.1 ml/$\mu$g) (7). Purified recombinant and native enzyme were analyzed by SDS-PAGE reducing gels (with 1× electrode running buffer) to determine approximate molecular weight. A 12% separating gel and 4% stacking gel were used. The recombinant enzyme was run with both reducing and non-reducing sample buffers.

PNP-Glycoside Assay:

Colorimetric assays were used to determine substrate specificity of the native and recombinant enzymes using the synthetic substrates: para-nitrophenol linked β-D-xyloside, α-D-mannoside, and β-D-glucuronide (FIG. 5). This assay determines specificity of enzymic release of p-nitrophenol from the three different sugars due to p-nitrophenylate formation (48). This assay was set up in a 96-well plate and read at 405 nm on a BIO-TEK Ceres 900 plate reader. Each reaction consisted of: 200 $\mu$l EPPS buffer (N-[2-hydroxyethyl]piperazine-N__-3-propanesulfonic acid), 50 mM, pH 8.0, 50 $\mu$l enzyme solution (containing various levels of enzyme protein), and 50 $\mu$l PNP-sugar solution, 5 mM. Blanks consisted of 200 $\mu$l EPPS buffer, 50 mM, pH 8.0, 50 $\mu$l PNP-sugar solution, 5 mM, and 50 $\mu$l PBS-Tween, pH 7.2, the same buffer used for the enzyme. The blanks allowed quantitation of non-enzymic hydrolysis of the PNP-sugars. The recombinant and native enzyme reaction mixtures and the blank reaction mixtures were incubated overnight at 30° C. The following morning, control wells were set up with β-D-xylosidase, α-D-mannosidase, and β-D-glucuronidase and their respective PNP-linked substrate. These substrate specific controls were incubated at 30° C. for four hours. Standards were set up and the assay was quantitated on a plate reader.

PNP-Carboxyl Ester Assay:

This assay determines specificity of enzymatic activity for five different PNP-fatty acid esters: PNP-acetate (2 carbon), PNP-propionate (3 carbon), PNP-butyrate (4 carbon), PNP-laurate (12 carbon), and PNP-palmitate (16 carbon). The assay was set up in a 96-well plate and read at 405 nm on a BIO-TEK Ceres 900 plate reader. Each reaction consisted of: 200 $\mu$l PBS buffer, pH 7.2; 50 $\mu$l PNP-ester solution, 0.77 mM; and 50 $\mu$l of enzyme (containing various levels of enzyme) added just prior to reading at 405 nm. Non-enzymic hydrolysis was measured in a solution that consisted of 200 $\mu$l PBS buffer, pH 7.2; 50 $\mu$l PNP-ester solution, 0.77 mM; and 50 $\mu$l PBS, pH 7.2, the buffer replacing the enzyme. Standard curves were obtained by measurement of the $A_{405}$ of solutions of known amounts of para-nitrophenol. This assay was read within 30 seconds in a single point manner as the enzyme works rapidly on this substrate.

PNP-Acetate Assay:

This assay was routinely used to determine enzymatic activity in samples of recombinant enzyme at the various steps in its expression and purification as described above, but with the PNP-acetate substrate only. This reaction was measured at pH=6.2 to 8.2. The PNP-acetate assay provides little color change at pH<6.2. At pH>8.2, non-enzymic hydrolysis obscures the enzyme catalyzed reactions.

GXM Degradation:

The enzyme samples were checked for activity on GXM specifically, in degradation reactions set up as follows: 10 $\mu$l of pure GXM (2 mg/ml) was incubated for 20 hours at 30° C. with 30 µl of enzyme sample (containing various levels of PNP-acetate activity). Controls were set up with only GXM and PBS buffer with no enzyme.

ELISA Assay for Quantitation of GXM Degradation: The products of the degradation reaction from above were quantitated by an ELISA protocol utilizing a capture antibody and indicator antibody. The 96-well plates were first coated and incubated overnight at 25° C. with the capture antibody, MAb 471. This is an anti-GXM monoclonal antibody. The buffer used for the overnight incubation was a phosphate coating buffer, 0.05 M sodium phosphate, pH 7.4, with EDTA. The plates were then washed with blocking buffer (0.05 M sodium phosphate, pH 7.4) and coated with blocking solution (blocking buffer with 0.05% Tween 20) for a 90 minute incubation at room temperature. The plates were washed with PBS-Tween. The degradation reaction from above, which constitutes the antigen for the capture antibody, was diluted 1:10,000 in wash buffer and added to the wells for a 90 minute incubation at room temperature. The plates were washed again with wash buffer and the indicator antibody, horseradish peroxidase (HRPO) labeled MAb 3C2, was added for a 90 minute incubation at ad room temperature. The MAb 3C2 was labeled by M. Grinsell of the University of Nevada following the Pierce protocol. The plates were washed with buffer and the BRPO substrate solution (TMB Microwell Peroxidase Substrate Solution Kirkegaard & Perry Labs, Inc.) was added for a 30 minute incubation at room temperature. The plates were read on the BIO-TEK Ceres 900 plate reader at 450 nm.

Hestrin Assay for Quantitation of Acetyl Groups on GXM:

The Hestrin assay was used to determine the quantity of acetyl groups found on GXM used for the above assays as well as Go that had been subjected to enzymatic degradation with the native enzyme by C. Savoy (29). The Hestrin assay consists of reacting the O-acetyl groups with hydroxylamine in alkali to form hydroxamic acids which produce a colored complex with $Fe^{3+}$ in acid solution. The degree of color formation relates the quantity of O-acetyl present and is determined by spectroscopy at 540 nm. Acetylcholine, 0.004 M, in 0.001 M sodium acetate, pH 4.5, is used for the standard.

Competition Assay: GXM vs. PNP-Acetate:

The PNP-acetate plate assay was conducted at a fixed PNP-acetate concentration of 0.333 mM and increasing amounts of GXM to determine any change in the rate of hydrolysis of the PNP-ester. This assay provided the apparent $K_m$ of the enzyme for GXM using an equation similar to the Michaelis Menton equation in the presence of a competitive inhibitor. GXM (2 mg/ml in PBS-Tween) was added in 50, 100, and 150 µl to decreasing amounts (in a substitutive manner) of 200 µl PBS-Tween. To this, 50 µl enzyme diluted in PBS-Tween, and 50 µl PNP-acetate, 5 mM, were added and the plate was read at 405 nm on. the BIO-TEK Ceres 900 plate reader. Enzyme controls were run with each amount of GXM, PNP-acetate, and no enzyme. Standards of para-nitrophenol were run at the same time.

Kinetics:

Kinetics of the enzyme were investigated through use of the PNP-acetate plate assay and the competition assay described above. The plates were read on the BIO-TEK Ceres 900 plate reader at 405 nm with a kinetic protocol that took readings every 20 seconds for 3 minutes. The results were analyzed to determine the apparent $K_m$ and $V_{max}$ parameters for both the native and recombinant enzymes with both PNP-acetate and GXM as their substrates.

EXAMPLE 5

PCR Screening of Mixed Unknown Genomes

Figure 6A:
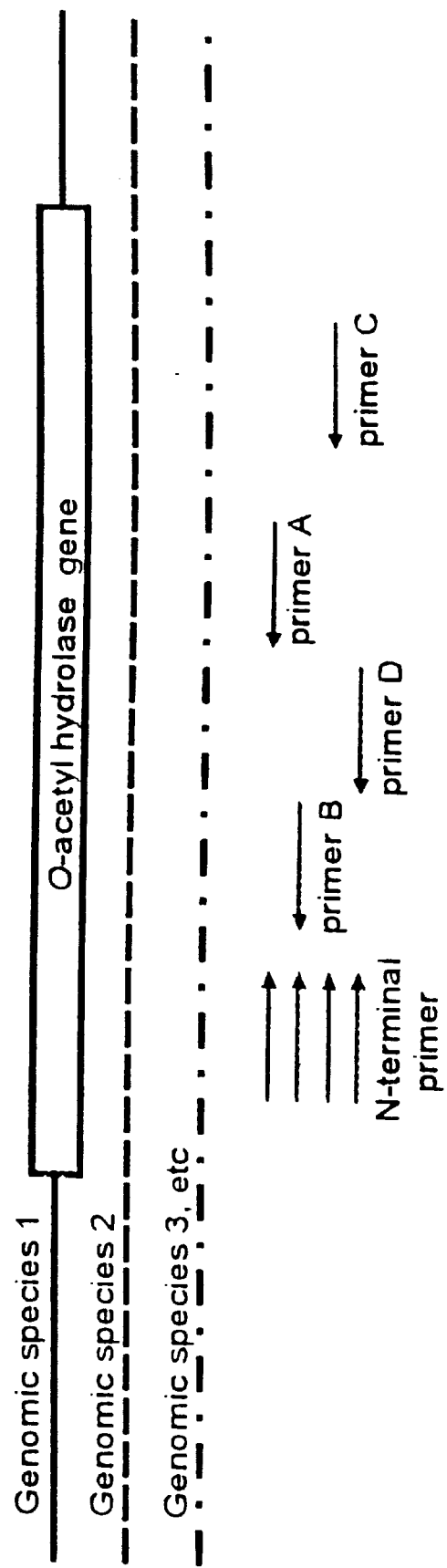
Figure 6B:
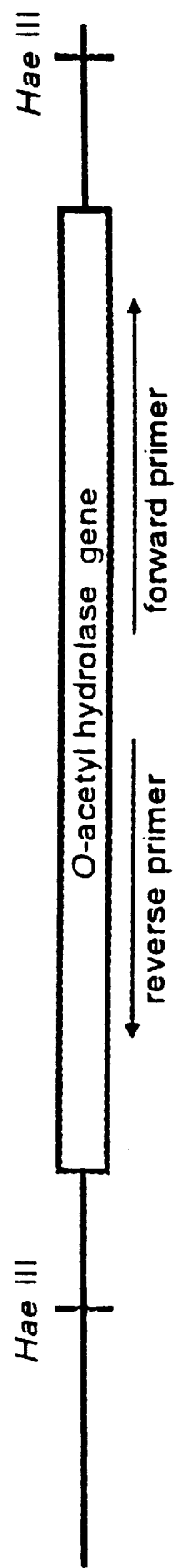
Figure 7A:
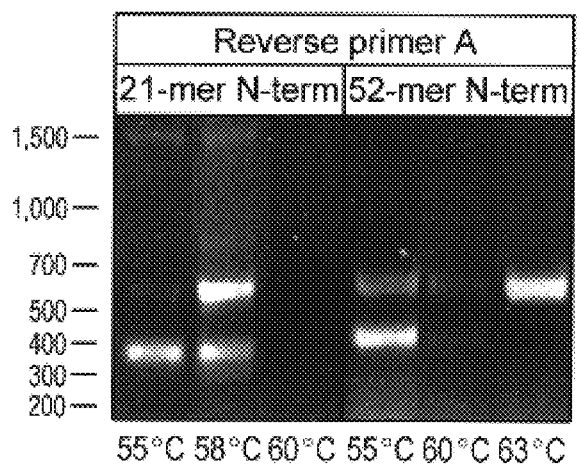
Figure 7B:
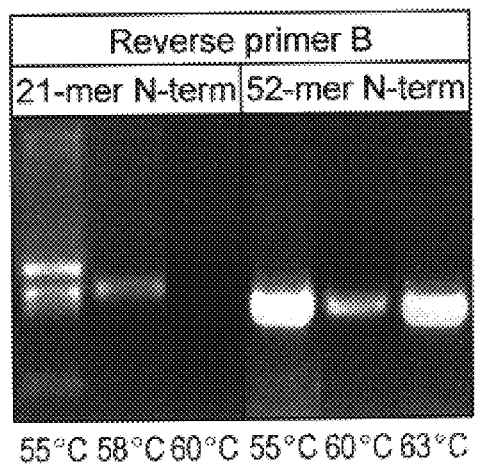
Figure 7C:
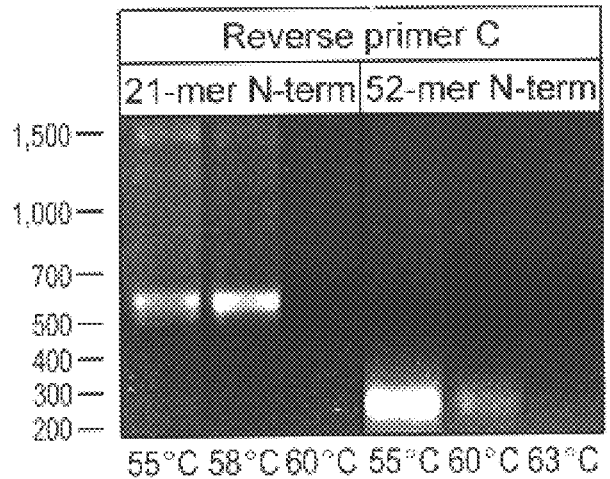
Figure 7D:
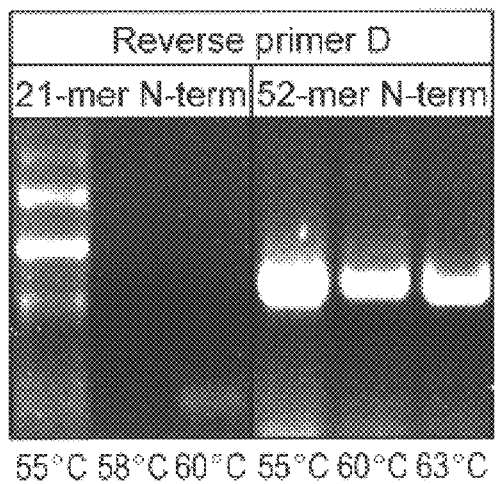

The screening strategy was first to screen the mixed genomes with degenerate primers designed from the amino acid sequences obtained through the peptide mapping, and second, to use the method of inverse PCR to obtain the start and stop codons of the gene (FIGS. 6A and 6B).

The peptide mapping results provided by the Core Protein Facility were analyzed to determine the best possible sequences for PCR primers. Favorable melting temperatures, terminal bases, self-annealing and hairpin formation were all taken into consideration. One N-terminal forward primer and four internal reverse primers were made according to Table 2. Although the species of the organism producing the protein was unknown, it was reasonably anticipated to be an aerobic bacterium. The first set of degenerate primers were therefore designed with the codon usage of enteric bacteria. The primer lengths were of 19 and 21 bases with one or two bases used in the third position (Table 2). The N-terminal 19-mer was used for initial PCR reactions and the 52-mer N-terminal for subsequent reactions, as seen in FIGS. 7A–7D. Reverse primers have reverse complement nucleotide and amino acid sequence shown in Table 2.

TABLE 2

Degenerate PCR Primers

| Type of primer | Nucleotide and Assosciated Amino Acid Sequence | |
|---|---|---|
| Screening PCR | | |
| N-terminal 19-mer | 5'GAC CCG GTT CCG GCW GGY G 3'<br>    D   P   V   P   A   G | (SEQ ID No. 7)<br>(SEQ ID No: 8) |
| N-terminal 52-mer | 5'GAC CCG GTT CCG GCW GGY GCW AAC CGT GCW<br>    D   P   V   P   A   G   A   N   R   A | |
| | 5' GCW GTT GCW GTW CCG CGT AAC 3'<br>    A   V   A   V   P   R   N | (SEQ ID No. 9)<br>(SEQ ID No. 10) |
| Internal 21-mer "A"<br>reverse complement | 5'RGT CGG GTG WAC GAA GTC CGG 3'<br>5'CCG GAC TTC GTW CAC CCG ACY 3'<br>    P   D   F   V   H   P   T | (SEQ ID No. 11)<br>(SEQ ID No. 12)<br>(SEQ ID No. 13) |
| Internal 21-mer "B" | 5'GTC RCC GTC WGC GTA ACG GGA 3' | (SEQ ID No. 14) |

TABLE 2-continued

Degenerate PCR Primers

| Type of primer | Nucleotide and Assosciated Amino Acid Sequence | |
|---|---|---|
| reverse complement | 5'TCC CGT TAC GCW GAC GGY GAC 3'<br>   S    R    Y    A    D    G    D | (SEQ ID No. 15)<br>(SEQ ID No. 16) |
| Internal 21-mer "C"<br>reverse complement | 5'CAG WGC GTT TTC WAC ACG GTC 3'<br>5'GAC CGT GTW GAA AAC GCW CTG 3'<br>   D    R    V    E    N    A    L | (SEQ ID No. 17)<br>(SEQ ID No. 18)<br>(SEQ ID No. 19) |
| Internal 21-mer "D"<br>reverse complement | 5'GTT GTT GAT CGG CAG GAT WGC 3'<br>5'GCW ATC CTG CCG ATC AAC AAC 3'<br>   A    I    L    P    I    N    N | (SEQ ID No. 20)<br>(SEQ ID No. 21)<br>(SEQ ID No. 22) |
| Inverse PCR | | |
| First half 29-mer (R)<br>reverse complement | 5'TTA ATG TCA TCC ACC TGT CCC TTG CTC AA 3'<br>5'TTG AGC AAG GGA CAG GTG GAT GAC ATT AA 3'<br>   L    S    K    G    Q    V    D    D    I | (SEQ ID No. 23)<br>(SEQ ID No. 24)<br>(SEQ ID No. 25) |
| Second half 20-mer (F) | 5' TC AAC AGC GCG GAA CAA ATC 3'<br>   FN   S    A    E    Q    I | (SEQ ID No. 26)<br>(SEQ ID No.27) |

Screening internal primers numbered A-D.
Inverse PCR primers labeled (R) reverse or (F) forward.
W=T or A
Y=T or C
R=A or G The first step of the PCR screening was to clone the interior of the gene with the N-terminal forward primer and the four different internal reverse primers. This process produced sporadic results marked by either too many bands or no bands on the agarose gel electrophoresis runs of the PCR products (FIGS. 7A–7D). The case of multiple bands was attributed to nonspecific binding, which was perhaps exacerbated by the presence of multiple genomes. The case of no bands was attributed to an annealing temperature in excess of the melting temperature of the primers. The difficulty of nonspecific binding was overcome by increasing the length of the N-terminal primer from 19 to 52 degenerate bases.

The experiment was repeated at increasing temperatures until loss of product occurred, again indicating the maximum melting temperature had been exceeded. The result of this experiment was a consistently placed band for three of the four internal reverse primers used: B, C, and D. FIGS. 7A–7D show the results of the 19-mer versus the 52-mer N-terminal primer when used with each of the internal reverse primers.

The following bands were excised from the gel for additional experiments: the two bands from the 52-mer 55° C. experiment, sized at approximately 400 and 600 base pairs; the single band from the 52-mer 63° C. experiment, sized a t approximately 500 base pairs; the single band from the 52-mer 55° C. experiment, sized at approximately 250 base pairs; and the single band from the 52-mer 63° C. experiment, sized at approximately 650 base pairs. These were excised, purified, and ligated into the pGEM T-Easy vector system in preparation for amplification of their sequences through transfection into E. coli and clonal expansion.

Initial sequencing reactions indicated that primer C closely followed the known N-terminal sequence. This is confirmed by the small size of the PCR product obtained with primer C. Primer C was not used for subsequent sequencing reactions for this reason. The same initial sequencing reactions ruled out the smaller PCR product resulting from primer A as a positive sequence, it is thought to be an artifact of the experiment.

Figure 8:
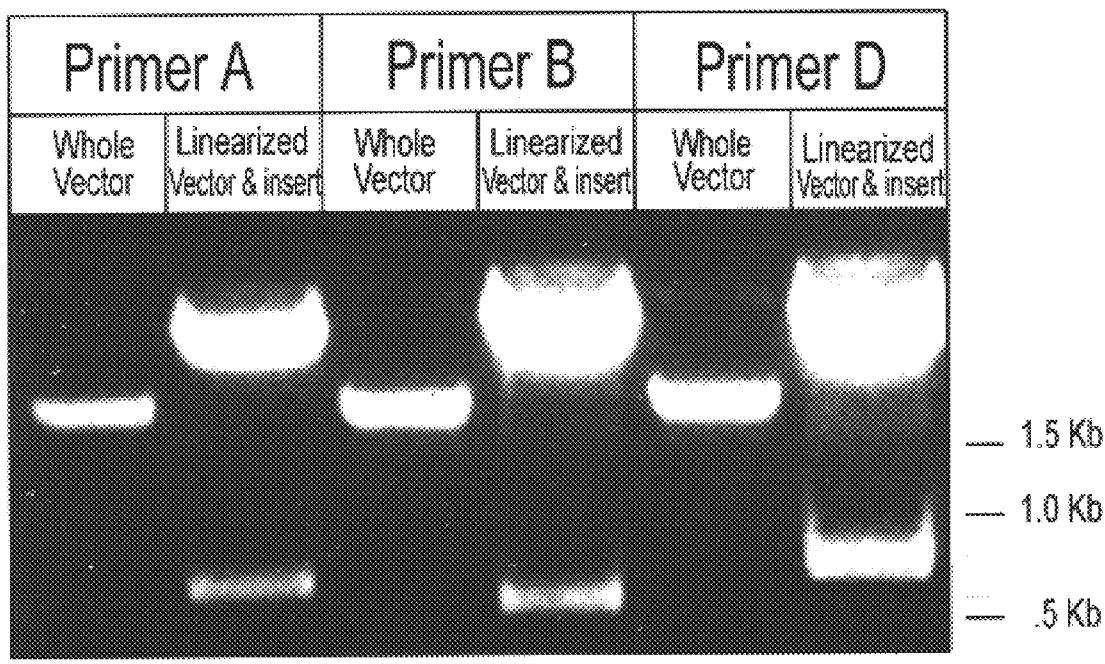

Recombinant vectors containing products of PCR with primers A, B, and D were isolated after transfection and growth. The vectors were restricted with EcoRI to confirm that products of proper length were incorporated (FIG. 8). The insert of recombinant vector A was approximately 600 base pairs. The insert of recombinant vector B was approximately 500 base pairs. The insert of recombinant vector D was approximately 650 base pairs. These matched well with initial results, and the inserts were prepared for the sequencing reaction.

Figure 9A:
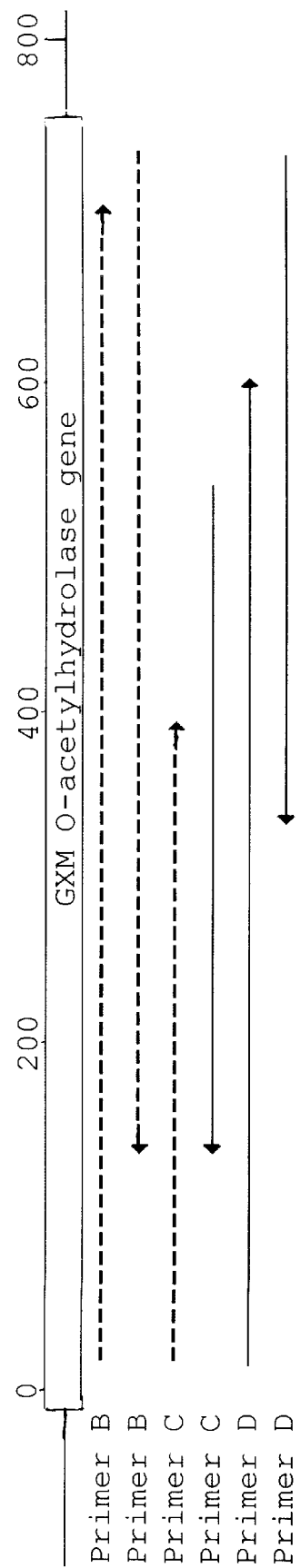

The nucleotide sequences of vector inserts A, B, and D were converted to protein sequence and aligned using DNAStar software (FIG. 9). The forward and backward sequencing reactions are outlined in FIG. 9A, and the nucleotide (SEQ ID No. 28) and deduced amino acid sequences (SEQ ID No. 29) are listed in FIG. 9B. The peptide sequences originally gained through peptide mapping are underlined with a solid line. The PCR primers are underlined with arrows indicating their direction. Sequencing in both the forward and reverse direction was accomplished with primers provided with the ABI sequencing kit. Much of the sequence was obtained in duplicate. Only known nucleotide sequence is listed; the amino- and carboxyl-termini remained unknown as they were obtained from degenerate primers. The deduced molecular mass of the protein was determined to be 24,145 Daltons.

Figure 10:
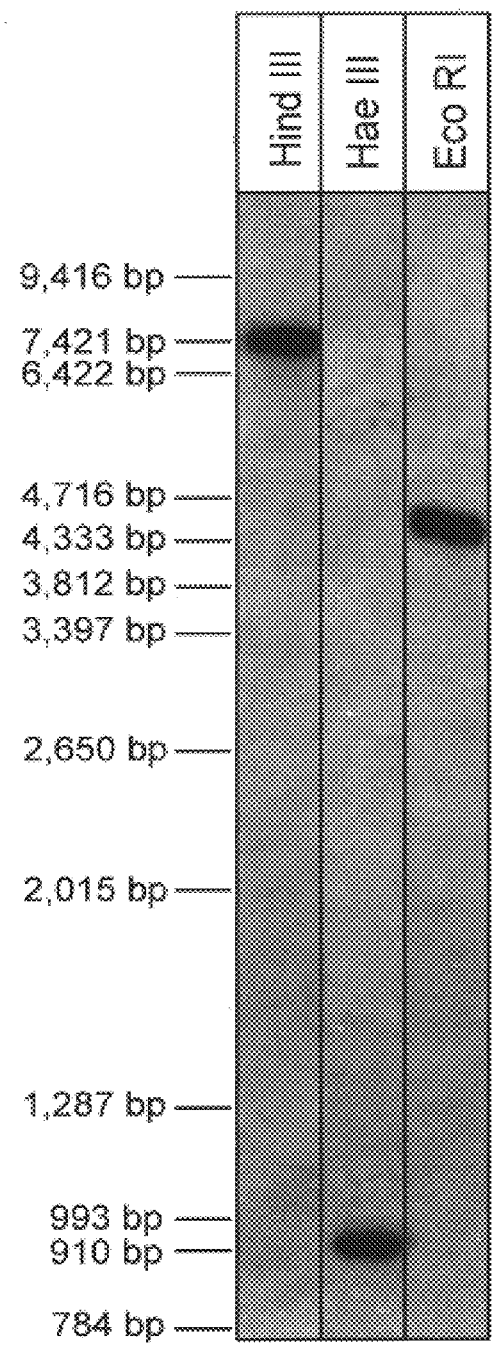

At this point, the amino and carboxyl termini needed to be sequenced as well. Conventional procedure would have been to pursue the creation and screening of a genomic or sub-genomic library. The number of species present in the culture, however, precluded this course of action. The culture had not been separated into individual species as they seemed to rely on the presence of the other species for survival. A southern blot was, however, performed in anticipation of creating a sub-genomic library. This blot indicated hybridization with an approximately 1 Kb Hae III fragment by the radiolabeled 52-mer N-terminal primer (FIG. 10). This information led to the next phase of the cloning of this gene, inverse PCR

EXAMPLE 6

Determination of Sequence at Amino and Carboxyl Termini Using Inverse PCR

Figure 11:
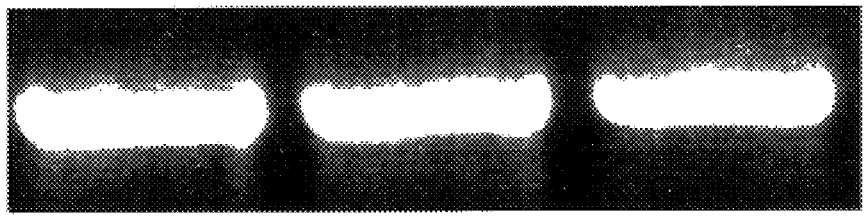

Genomic DNA was restricted using Hae III and separated by agarose gel electrophoresis. The bands in the size range of 900–1000 base pairs were excised and prepared. These were ligated to form circular DNA and then run through PCR with outward facing primers that had been designed to hybridize to the central region of the gene (Table 2). The PCR products were separated by agarose gel electrophoresis and are pictured in FIG. 11. The products appear to weigh approximately 850–900 base pairs. The expected weight was calculated by deducting the amount of genomic DNA not included in the area being cloned (the DNA falling between the two outward facing PCR primers) from the approximate full plasmid weight of approximately one kb and was determined to be of about 900 base pairs. As the products were in agreement with expected values, they were sequenced. The sequence obtained included start and stop sites and is shown in FIGS. 12A–12C (nucleotide sequence: SEQ ID No. 30; deduced amino acid sequence: SEQ ID No. 31). This concludes the experiments leading to the acquisition of the full sequence of the gene for this novel GXM-O-acetylhydrolase. The next phase of the project was to express the recombinant protein in *E. coli*.

EXAMPLE 7
Homology Search

The BLAST homology search produced no exact matches for the gene sequence attained, although it did have very high scores of 108–113 bits for five different platelet-activating factor acetylhydrolases: rat β (57, SEQ ID No. 32), human β (2,21, SEQ ID No. 33), mouse β (3, SEQ ID No. 34), human γ (1. SEQ ID No. 35), bovine γ (22,28, SEQ ID No. 36), and rat γ (3, SEQ ID No. 38) (FIG. 13, mouse γ, SEQ ID No. 37; native, SEQ ID No. 31). The E-values (similar to probability values) are also very high and range from 1e-23 to 4e-25, indicating the expected number of hits when searching the database used. Identities, the fraction of the identical residues between query and database, were all scored at 35%. Positives, the fraction of residues for which the alignment scores had a positive value, ranged from 54–58%.

The PSORT search indicated a possible cleavage site at amino acid 21, which just precedes the original N-terminus determined by peptide sequencing. PSORT also stated that the protein seems to have a cleavable N-terminal signal sequence. The program determined there was a high probability the protein would be targeted to either the periplasmic space or the outer membrane of its native bacteria. The algorithm requested information on whether the bacteria that expressed the native protein was Gram positive or Gram negative. As this was unknown, due to the mixed, unknown status of the original sewage bacterial culture, each Gram status was entered. More information was available when the originating bacteria species was assigned gram-negative status rather than gram-positive.

EXAMPLE 8
Preparation of Vector and Insert

Figure 14:
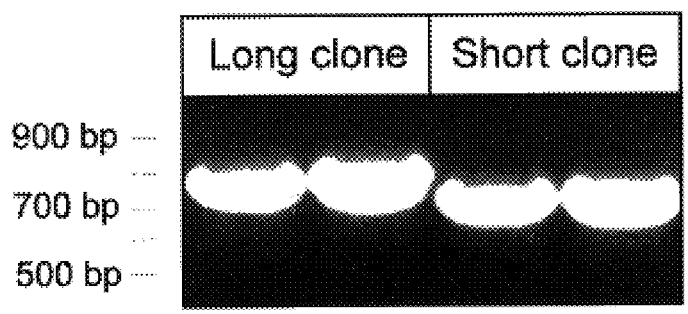
FIG. 14 shows agarose gel electrophoresis of PCR products prepared for pET expression vector insertion.

The vector and insert for the expression plasmid were prepared. PCR was used to create primers that added BamHI and NdeI restriction enzyme sites for insertion into the pET expression plasmid and to place the coding region of the gene in the proper reading frame (Table 3). Mutated nucleotides are underlined. Reverse primers have reverse complement nucleotide and amino acid sequence. Two clones were made, a long and a short one. The long clone included the purported signal target sequence and the short clone did not. The PCR products were separated on a 1% agarose gel electrophoresis (FIG. 14), the long insert appeared to be of approximately 750 base pair and the short insert appeared to be of approximately 700 base pair, as expected. The PCR products were spin column purified and quantitated by absorption spectroscopy at 260 nm. The concentration of the inserts ranged from 36.3 to 46.2 ng/μl.

TABLE 3

PCR Primer Design for Expression Vector

| Type of primer | Nucleotide and Associated Amino Acid Sequence | |
|---|---|---|
| Forward: *Nde* I site added | | |
| Long clone, 45-mer: Genomic | 5' GGA AAA <u>CATATG</u> AAT AAA CTG CAT CTT sequence: | 5' GGA AAA ATC ATG AAT AAA CTG CAT CTT |
| Amino acid sequence: |               M   N   K   L   H   L | |
| | GTC ATT AGC GTT CAA CTG 3' | (SEQ ID No. 39) |
| | GTC ATT AGC GTT CAA CTG 3' | (SEQ ID No. 40) |
| |  V   I   S   V   Q   L | (SEQ ID No. 41) |
| Short clone, 36-mer: Genomic sequence: Amino acid sequence: | 5' GT TCG TTG <u>CATATG</u> GCG GAA ACC ATC<br>5' GT TCG TTG TTA GCG GCG GAA ACC ATC<br>5'     S   L   L   A   A   E   T   I | |
| | TAT CAG GAT C 3' | (SEQ ID No. 42) |
| | TAT CAG GAT C 3' | (SEQ ID No. 43) |
| |  Y   Q    D C 3' (SEQ ID No. 44) | |
| Reverse: *Bam*HI site added | | |
| Long and short clone used same 34-mer: Genomic sequence: Reverse complement: Amino acid sequence: | 5' GT AAC <u>GGATCC</u> TTT TTT CGG CGC GTA TTT<br>5' GT AAC GCA TTA TTT TTT CGG CGC GTA TTT<br>5' TC AAC AAA TAC GCG CCG AAA AAA TAA TGC<br>5'     N   K   Y   A   P   K   K     C | |

TABLE 3-continued

PCR Primer Design for Expression Vector

| Type of primer | Nucleotide and Associated Amino Acid Sequence | |
|---|---|---|
| | GTT GA 3' | (SEQ ID No. 45) |
| | GTT GA 3' | (SEQ ID No. 46) |
| | GTT AC 3' | (SEQ ID No. 47) |
| | V 3' (SEQ ID No.48) | |
| Nde I restriction site: | 5'-CA↓TA TG-3' | (SEQ ID No. 49) |
| | 3'-GT AT↑AC-5' | |
| BamHI restriction site: | 5'-G↓GATC C-3' | (SEQ ID No. 50) |
| | 3'-C CTAGT↑G-5' | |

The vector and insert were digested with the restriction enzymes BamHI and NdeI. The double digestion allowed for proper orientation of the insert within the vector. The digested vector and insert were separated on a 1.2% agarose gel electrophoresis, excised, and purified. Quantitation by spectroscopy at 260 nm showed both vector and insert to be present at approximately 9.9 ng/μl, a low, but usable, concentration for the next step of ligation.

Figure 15:
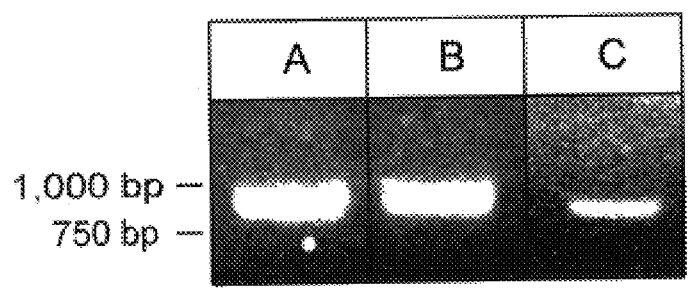
FIG. 15 shows agarose gel electrophoresis of colony PCR screening of recombinant pET28a(+) transformants.

The vector and insert were ligated and transformed into the non-expression host, E. coli Novablue competent cells. Three transformants were found, two with the long insert and one with the short insert through use of the colony PCR (FIG. 15). These were grown up in LB broth overnight and the plasmid DNA isolated by miniprep. Quantitation by spectroscopy at 260 nm showed plasmid DNA present in concentrations ranging from 8.3–24.8 ng/μl. The plasmids were transformed into the expression host, E. coli strain BL21 and plated for overnight growth at 37° C.

Figure 16:
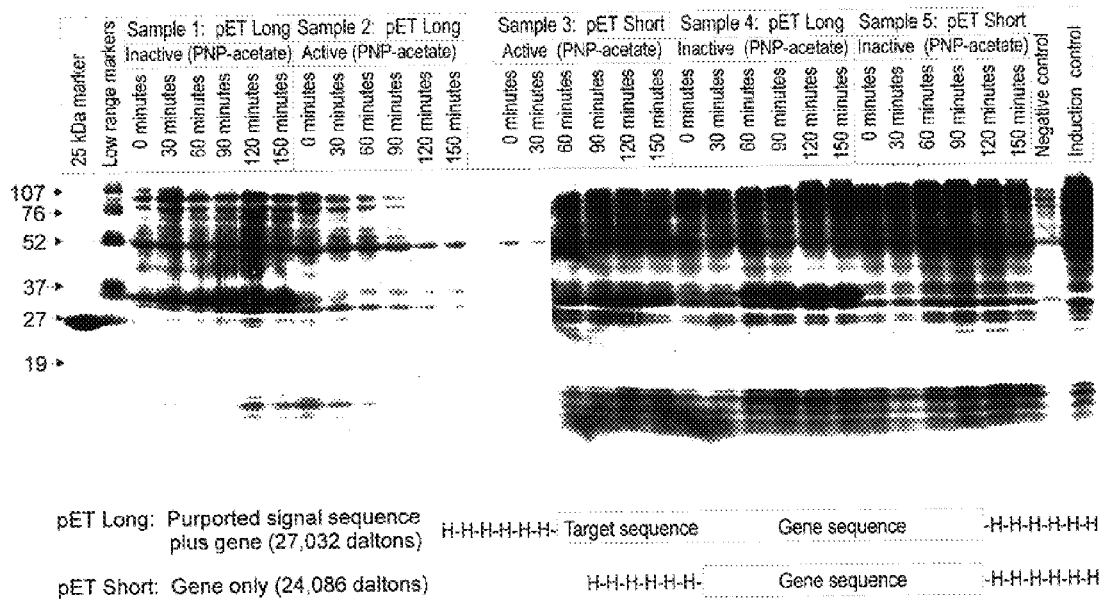
FIG. 16 shows SDS-PAGE of time course of induction experiment with results of PNP-acetate assays.

The following day, 100 ml cultures of LB-Kan were inoculated from these plates. The cultures were induced after attaining appropriate growth and samples removed every 30 minutes, to determine the time course of induction. The samples were separated by SDS-PAGE and tested for enzymatic activity with the PNP-acetate assay (FIG. 16). The SDS-PAGE is difficult to decipher as it is of a crude cell extract and many proteins are present. There does appear to be an increasing concentration of protein of approximately 28–30 kDaltons in samples 1, 3, and 4 on the SDS-PAGE. The presence of these proteins may be attributable to induction of the pET plasmid, and the somewhat larger size of these in comparison to the native enzyme may be attributable to the presence of a 12× Histidine tag on the recombinant protein. Only samples 2 and 3, however, proved to be enzymatically active on the PNP-acetate substrate.

Sample 3 of FIG. 16 was chosen for affinity purification as it was enzymatically active on PNP-acetate and it was a short clone. The short clone was used for the first attempt at purification as the molecular weight more closely resembled that of the native enzyme and the purported target signal sequence seemed unnecessary as expression was being conducted in a species other than the native. Purifying a long clone has not been ruled out as a possible future experiment. Aliquots of 1.5 ml were collected from the $Ni^{2+}$ column purification starting with the addition of the crude cellular extract. The aliquots were combined into 4.5 ml samples and were tested for enzymatic activity after being dialyzed into 1×PBS-Tween. The sample taken following the elution buffer proved to have the highest activity. For this reason, it was used for all the characterization assays.

Figure 17:
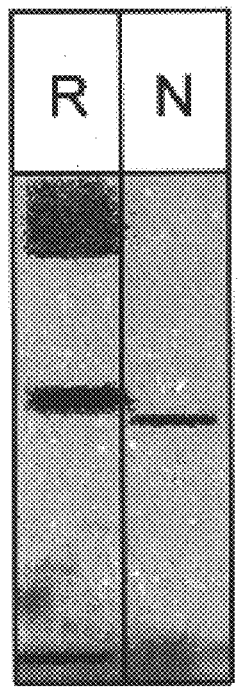
FIG. 17 shows SDS-PAGE purified recombinant.

EXAMPLE 9
Quantitation of Purified Recombinant Enzyme and Approximation of Molecular Mass The sample was determined to have a protein concentration of 32.2 μg/ml using the BCA method. Absorption spectroscopy at 280 nm indicated an approximate concentration of 57 μg/ml. The native enzyme provided for comparative assays was determined to have a protein concentration of 9.58 μg/ml with the BCA method. However, when the two enzymes were used in side-by-side assays with identical volumes, the native proved more active at all concentrations of substrate. For this reason, it is thought the recombinant is not entirely pure and that the protein assay contains contaminants. The estimation of concentration, therefore, is an overestimate of the actual value. SDS-PAGE of the purified recombinant enzyme resulted in more than one band (FIG. 17). The most prominent band appeared to be slightly larger than that of the native enzyme, which was analyzed at the same time. The difference in size is attributed to the presence of the 12× histidine tag on the recombinant. The native, whose mass was determined by mass spectrometry to be 24,866 Daltons, is the standard for this gel.

EXAMPLE 10
PNP-Glycoside Assay

This assay was used first to determine if the enzyme was active on any of the sugar components of GXM: glucuronide, xyloside, or mannoside. Both the recombinant and native enzymes failed to cause any hydrolysis of the PNP-sugar substrates (Table 4). The glycosides were used in concentrations that had been proven optimal in diagnostic assays with PNP-acetate. α-D-mannosidase, 13-D-xylosidase, and β-D-glucuronidase were used as controls to ensure substrates were reactive. These controls were all positive, confirming that the substrates are reactive.

TABLE 4

Results of para-Nitrophenol-Substrate Assays in Terms of Well Absorbances at 405 nm and the Amount of Substrate Converted to nmols.

| | Native Enzyme | | Recombinant Enzyme | |
|---|---|---|---|---|
| Para-Nitrophenol-Substrate | $A_{405}$ (mOD) | Substrate Converted (nmol) | $A_{405}$ (mOD) | Substrate Converted (nmol) |
| PNP-α-D-mannoside | 0 | 0 | 0 | 0 |
| PNP-β-D-xyloside | 0 | 0 | 0 | 0 |
| PNP-β-D-glucuronide | 0 | 0 | 0 | 0 |
| PNP-acetate | 0.441 | 12.41 | 0.436 | 12.27 |
| PNP-propionate | 0.019 | 0.76 | 0.003 | 0.32 |
| PNP-butyrate | 0 | 0 | 0.012 | 0.57 |
| PNP-laurate | 0.001 | 0.26 | 0.007 | 0.43 |

TABLE 4-continued

Results of para-Nitrophenol-Substrate Assays in Terms of Well Absorbances at 405 nm and the Amount of Substrate Converted to nmols.

| Para-Nitrophenol-Substrate | Native Enzyme | | Recombinant Enzyme | |
|---|---|---|---|---|
| | $A_{405}$ (mOD) | Substrate Converted (nmol) | $A_{405}$ (mOD) | Substrate Converted (nmol) |
| PNP-palmitate | 0 | 0 | 0 | 0 |

EXAMPLE 11
PNP-Carboxyl Ester Assay

This assay was used to see which acyl chain length ester the enzyme would be most active in hydrolyzing. PNP-linked esters ranging from 2 carbons to 16 carbons were tested. Both the recombinant and the native enzyme were most active on the PNP-acetate substrate (Table 4). There was some small amount of activity for the other substrates, but it was very near zero.

EXAMPLE 12
PNP-Acetate Plate Assay for De-Acetylation Activity

Figure 18:
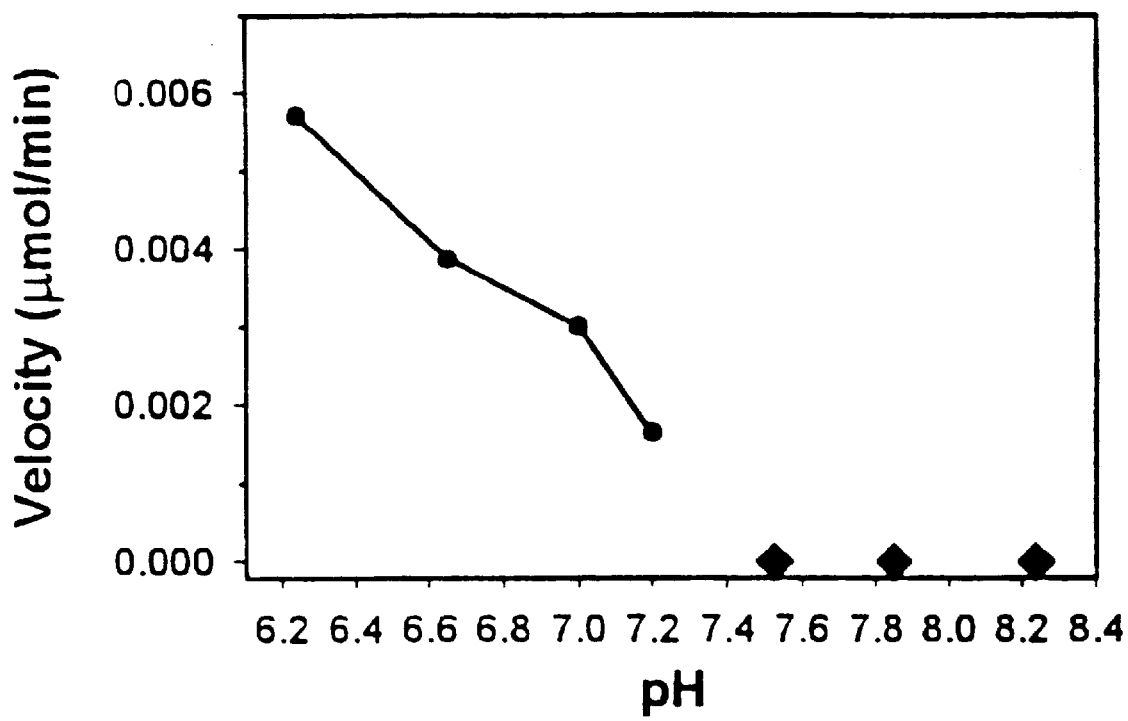
FIG. 18 shows pH profile of recombinant enzyme with PNPA substrate.

A quantitative determination of the rate of substrate hydrolysis was desired at this point. The effect of hydrogen ion concentration on the reaction was first investigated. PNP-linked substrates are hydrolyzed most effectively at basic pH, with color chance being detectable down to pH=6. The enzyme, however, was originally found in bacteria that required a slightly acidic medium for optimal growth. The enzyme became more active as pH was decreased (FIG. 18), however, the PNP-acetate assay was not able to detect activity below pH=6. As a consequence, the optimal [H$^+$] was not determined. FIG. 18 shows that the optimal would be in the acidic region. The three points designated by diamonds in FIG. 18 represent reactions that had velocity indistinguishable from non-enzymic hydrolysis. There is activity at pH=7.2. As all diagnostic assays had been conducted at pH=7.2 thus far, and pH=7.2 seems suitable for both the enzyme activity and the assay needs, and is relevant to eventual in vivo use of the enzyme. All of the following assays were conducted at pH=7.2.

EXAMPLE 13
GXM Degradation Quantitated by Hestrin

The next phase of the project confirmed the presence of acetyl ester groups on GXM, as well as the loss of acetyl ester groups during degradation with the enzyme. The Hestrin assay was used for this purpose. The GXM of serotype A strain CN6, which was used exclusively throughout this study, was determined to contain approximately 13.6% (w/w) acetyl ester groups. The loss of acetyl ester groups during degradation with the native enzyme was confirmed by Hestrin assay conducted by C. Savoy. GXM was degraded overnight by both the recombinant and native enzymes. The Hestrin assay was used to quantitate the loss of acetyl ester groups. The native enzyme reduced the amount of acetyl ester groups by 96%. The recombinant reduced the amount of acetyl ester groups by 91%.

EXAMPLE 14
PNP-Acetate Plate Assay

Figure 19A:
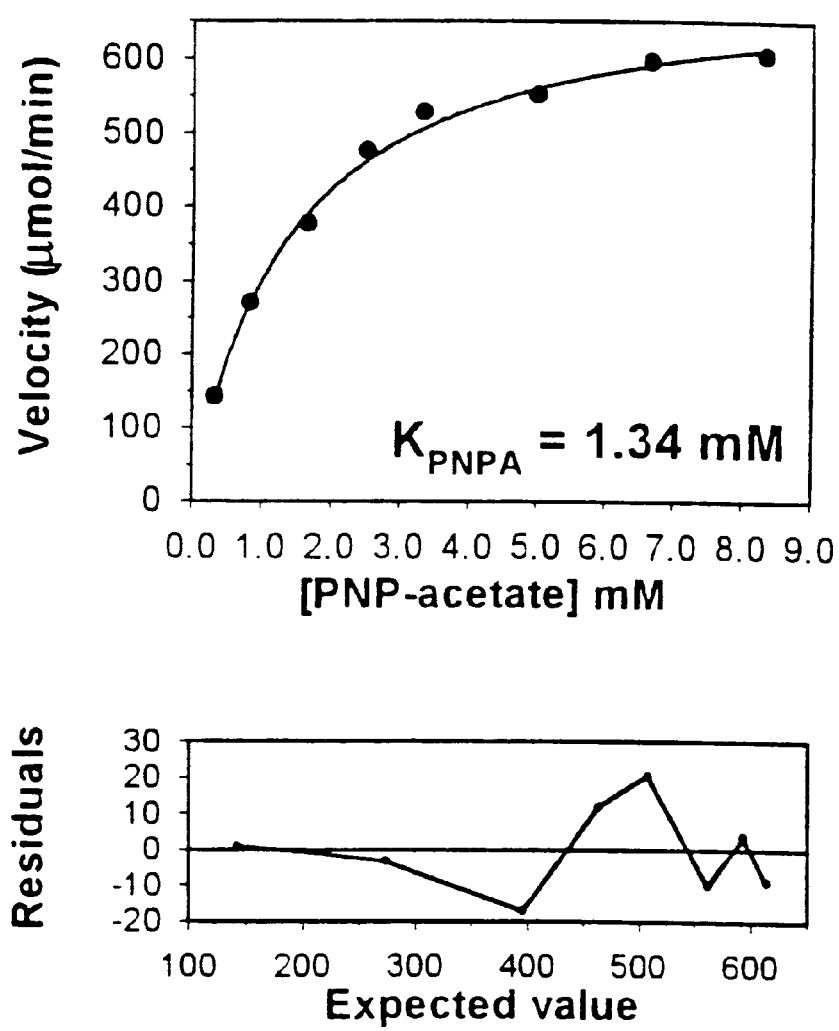

The $K_m$ and $V_{max}$ of the recombinant and native enzymes for the PNP-acetate substrate were determined by an experiment, in which the amount of enzyme was held constant while the amount of PNP-acetate was increased. The velocity of the reaction at the various concentrations of PNP-acetate was plotted against the time of the reaction on Sigma Plot (FIGS. 19A and 19B). The $V_{max}$ and $K_m$ were determined through a single hyperbolic regression:

$$y = \frac{ax}{b+x},$$

which is comparable to the Michaelis Menton equation (48):

$$V = \frac{V_{max}S}{K_m + S},$$

where S is the concentration of PNP-acetate used in the assay, Vmax is the maximum velocity attained in the reaction, and Km is the concentration of substrate required for the reaction to reach half maximal velocity. The recombinant and native enzymes were found to have very similar $K_m$ values, 1.34 mM±0.10 and 1.26 mM±0.29, respectively: This indicates that, not only do both enzymes prefer PNP-acetate as a substrate, but their reactions are very similar, kinetically. The $K_m$ and $V_{max}$ for the PNP-acetate substrate will be referred to as $K_{PNPA}$ and $V_{PNPA}$ from this point.

EXAMPLE 15
Competition Assay: GXM vs PNP-Acetate

The last experiment conducted was designed to determine the $K_m$ of the recombinant and native enzymes on GXM ($K_{GXM}$) This was accomplished by competing the two substrates, PNP-acetate and GXM, in a reaction with the enzymes. The concentration of PNP-acetate and enzyme was held constant while the concentration of GXM was varied. The enzyme concentration was held constant. This produced a plot where velocity of PNP-acetate hydrolysis decreased as the concentration of GXM increased (FIG. 20). This plot was regressed with a hyberbolic inhibition formula:

$$y = \frac{ab}{b+x},$$

where a is the velocity of PNPA hydrolysis in the absence of GXM, b is the value of $EC_{50}$, x is the concentration of GXM and y is the reaction velocity. $EC_{50}$ is the concentration of GXM which decreases PNPA hydrolysis to 50% of that in the absence of GXM. Consider the Michaelis and Menton equation for the reaction in the presence of a competitive inhibitor:

$$v = \frac{V_{max}[S]}{K_m\left(1 + \frac{I}{K_I}\right) + [S]}.$$

In the case of competitive substrates, the equation becomes:

$$v = \frac{V_{PNPA}[PNPA]}{K_{PNPA}\left(1 + \frac{EC_{50}}{K_{GXM}}\right) + [PNPA]}.$$

The value for $EC_{50}$ is used to calculate $K_{GXM}$ using the following equations:

$$v = \frac{V_{max}[S]}{K_m + [S]} \quad (1)$$

$$\frac{v}{2} = \frac{V_{max}[S]}{K_{PNPA}\left(1 + \frac{EC_{50}}{K_{GXM}}\right) + [S]} \quad (2)$$

Dividing equation (1), the Michaelis and Menton classic equation, by equation (2), the Michaelis and Menton equation for rate in presence of competitive inhibitor at half velocity, provides the solution for $K_{GXM}$:

$$K_{GXM} = \frac{EC_{50}}{\left(1 - \frac{[S]}{K_{PNPA}}\right)}$$

$K_{PNPA}$ was calculated from the results shown in FIGS. 19A and 19B and [S] was the amount of substrate used in all the reactions. This analysis yielded the $K_{GXM}$ of the recombinant and native enzymes of 1.45 mM±0.19 and 0.60 mM±0.01 respectively. These are of the same order of magnitude with each other and with the $K_{PNPA}$ values. These similarities indicate that the two enzymes see GXM as a substrate which is just as acceptable as PNP-acetate and that their reactions are kinetically, very similar.

Discussion

The objective of this study was to produce a recombinant clone of a novel enzyme that de-O-acetylates GXM. The native protein was originally isolated and purified in the Kozel laboratory -by Houpt and Savoy from bacteria that were cultured from a sewage sample and subjected to peptide mapping. The peptide mapping produced partial sequences which were used to develop PCR primers for screening genomic DNA from the mixed culture for the gene of the enzyme.

All evidence indicates that the expressed recombinant enzyme is a clone of the native GXM-O-acetylhydrolase. First, the nucleotide sequence (FIGS. 12A–12C) matched what was known of the native enzyme's peptide sequence. The final full gene sequence attained, which contained both start and stop codons, was translated to a protein sequence. This protein sequence contained, in 100% agreement, the original peptide sequences. Second, the recombinant enzyme has the same substrate specificity as the native enzyme. They are GXM-O-acetylhydrolases, as shown by the synthetic p-nitrophenol substrate assays. Third, the two enzymes have similar kinetic parameters in reactions with the two substrates, PNPA and GXM. Finally, the deduced molecular mass of the full sequence protein was determined to be 27,032 Daltons. This mass value was slightly higher than that of the native protein, which had been determined to be of approximately 24,866 Daltons through mass spectroscopy by the Core Protein Facility of the University of Nevada.

The homology search conducted through BLAST failed to reveal a complete match for the protein, indicating this is likely a novel protein. A number of platelet activating factor (PAF) acetylhydrolases, however, were produced as matches with a high degree of similarity, as shown in FIGS. 13A and 13B. This confirmed that the protein sequenced should have an acetylhydrolase type activity.

Platelet-activating factor acetylhydrolases are the key inactivators of PAF and play an important role in development (22,56). As PAF is a mammalian protein, these enzymes are found only in mammals. The enzymes are heterotrimeric and consist of 29, 30, and 45-kDa subunits. The 29-kDa subunit, referred to as the gamma subunit, has been shown to be catalytically active in *E. coli* when expressed without the other two subunits (22). The sequence of the GXM-O-acetylhydrolase was highly homologous to human, mouse, and bovine PAF-acetylhydrolases of both subunits 29- and 30-kDa.

The various PAF acetylhydrolases listed in the BLAST search share active site residues. This information on the active site residues may provide a future direction for this research, e.g. mutational analysis, when a higher level of characterization of the enzyme is desired.

The PSORT search also provided information that may lead to identification of the species from which this protein originates. The information was in the form of a greater degree of PSORT response when declaring the species of origin to be Gram-negative rather than Gram-positive. The program had very little information to offer when the originating species was declared to be Gram-positive, whereas much information was available when declaring the originating species to be Gram-negative. This is more interesting when coupled with Gadebusch's experience of isolating a likely mixed GXM-hydrolase from the Gram-negative species Alcaligenes sp. S-3723 (17). Future investigation into the species of origin could logically center around the hypothesis that the species being sought will be Gram-negative.

PSORT also identified a possible signal target sequence comprising the first 21 amino acids of the protein. The suggested cleavage site falls just prior to the first N-terminal residue identified through the peptide mapping. The deduced molecular mass of the protein without this signal sequence is 24,086 Daltons, which is much closer to the mass of the native protein, 24,866. There is a possibility that the active form of the native enzyme is the cleaved form. The proposed site of signal sequence targeting is the periplasm. This agrees with previous findings in the Kozel laboratory that the native enzyme was not found in the media of its native culture and appears to be confined to the cell.

Two assays proved that both the recombinant and native enzymes hydrolyze the O-acetyl groups from glucuronoxylomannan: the ELISA capture antibody assay and the PNPA versus glucuronoxylomannan kinetic assays. The ELISA is useful in proving that this specific hydrolysis is occurring as the O-acetylation on glucuronoxylomannan forms part of the antigenic epitope for some monoclonal antibodies. Without the O-acetylation in that epitope, the MAb is unable to bind glucuronoxylomannan. This absence of binding is indicated by a loss of color in the ELISA assay. The experiments on the effect of glucuronoxylomannan on PNPA activity showed a decrease in PNPA activity at all concentrations of glucuronoxylomannan used. This decrease is due to the recombinant and native enzymes both preferentially binding glucuronoxylomannan over PNPA. This decrease was quantitated using kinetic calorimetric assays and Michaelis and Menton equations for reaction rates in the presence of competitive inhibitors. The K. values for the two enzymes on glucuronoxylomannan were determined to be of the same magnitude.

Polysaccharide degrading enzymes and their use against human pathogens have been investigated for several microorganisms. Enzymes were discovered that could degrade the polysaccharide capsules of both *S. pneumoniae* and *C. neoformans*, although it doesn't appear that extensive purification or kinetic studies of-these enzymes were performed. The first studies were done in the. 1930's by Avery and Dubos, who discovered a bacteria that could degrade the capsular polysaccharide of Type III Pneumococcus (4,5,15).

They showed this activity was due to an enzyme, which they successfully isolated from the bacteria. The enzyme was used for in vitro as well as in vivo studies. Avery and Dubos showed that this enzyme degrades the capsular polysaccharide of Type III Pneumococcus under three conditions: first, as soluble polysaccharide in vitro, second, from living organisms growing in media, and third, in the animal body (5). The in vivo studies in mice not only proved protection against infection was a result of pre-treatment with enzyme, but also that some positive effect resulted from enzyme treatment in mice already infected with the Type III Pneumococcus (5).

In 1960, Gadebusch reported the discovery of an enzyme that degraded the capsular polysaccharide of *C. neoformans*. In addition to conducting experiments similar to Avery and Dubos (with similar results), Gadebusch expanded his investigation to assess the effect of capsule degradation on the pathogenicity of *C. neoformans* (17–20). Cells partially decapsulated by incubation with the enzyme were used to immunize mice. The partially decapsulated cells stimulated both agglutinins and protective antibodies in vivo. Antisera from these experiments were shown to be effective in protecting mice against a lethal injection of encapsulated cells (18).

These early studies show that these enzymes have potential to be therapeutic agents against *C. neoformans*. In addition, a recombinant enzyme can be used as a tool for conducting further studies of *C. neoformans* and glucuronoxylomannan. First, a recombinant enzyme could be used to study of the pathogenicity of *C. neoformans* in both in vivo and in vitro models. The effect of de-O-acetylation of the capsular polysaccharide on pathogenicity is unknown at this time. Also, as the enzyme can reliably modify a n antigenic epitope of glucuronoxylomannan, it can be exploited to study the epitope. Lastly, little is known of the structural requirements for the various biological activities of GXM. This recombinant enzyme can be used as a tool to elicit structure-function relationships of the polysaccharide.

In the short-term, a large scale expression and purification protocol will be developed so that more extensive kinetic studies can be carried out. There is a need for a larger supply of recombinant to conduct these studies. Purity is required to determine the specific activity of the recombinant. Once these issues are addressed, the enzyme can be more fully characterized in terms of its kinetic parameters: specific activity, turnover number ($k_{cat}$) and specificity ($k_{cat}/K_m$)

The O-acetylhydrolase is known to be part of a complex of at least four enzymes that work together to completely degrade GXM. An additional goal for the future is to finally purify the other three enzymes and ultimately create a working complex of all four recombinant enzymes. This complex could someday be used not only as a tool to study the pathogenicity of *C. neoformans* and its capsular polysaccharide, but also to provide a therapeutic agent for patients suffering from cryptococcal meningitis.

The following references were cited herewith.

1. Adachi, et al., 1995. Biochim.Biophys.Acta. 214:180–187.
2. Adachi, et al., 1997. Biochem.Biophys.Res.Commun. 233:10–13.
3. Albrecht, et al., 1996. Dev.Biol. 180:579–593.
4. Avery, et al., 1930. Science 72:151
5. Avery, et al., 1931. J. Exp. Med. 54:73–89.
6. Bennett, et al., 1977. Am. J. Epidemiol. 105:582–586.
7. Bollag, et al., 1996. Protein Methods. p.57–79. Wiley-Liss, Inc., New York.
8. Bottone, et al., 1987. J. Infect. Dis. 156:242
9. Breen, et al., 1982. Infect.Immun. 36:47–5 1.
10. Bulmer, et al., 1967. J.Bacteriol. 94:1480–1483.
11. Bulmer, et al., 1968. J. Bacteriol. 95:5–8.
12. Bulmer, et al., 1967. J.Bacteriol. 94:1475–1479.
13. Casadevall, et al., 1998. *Cryptococcus neoformans*. American Society for Microbiology, Washington, D.C.
14. Cherniak, et al., 1998. Clin Diagn Lab Immunol 5 (2): 146–159.
15. Dubos, et al., 1931. J. Exp. Med. 54:51–71.
16. Fromtling, et al., 1982. Mycopathologia 79:23–29.
17. Gadebusch, 1960a. J. Infect. Dis. 107:402–405.
18. Gadebusch, 1960b. J. Infect. Dis. 107:406–409.
19. Gadebusch, et al., 1960. Naturwissenschaften 47:329–340.
20. Gadebusch, et al., 1961. Can. J. Microbiol. 7:53–60.
21. Hattori, et al., 1995. J. Biol. Chem. 270:31345–31352.
22. Hattori et al., 1994. J. Biol. Chem. 269:23150–23155.
23. Hirano, et al., 1964c. Arch. Neurol. 11:386–397.
24. Hirano, et al., 1964a. Am. J. Pathol. 45:1–19.
25. Hirano, et al., 1964b. Am. J. Clin. Pathol. 45 :195–207.
26. Hirano, et al., Arch. Neurol. 12:189–196.
27. Hirano, et al., 1965b. J. Neuropathol. Exp. Neurol. 24:386–397 .
28. Ho, et al., 1997. Nature 385:89–93.
29. Kabat, et al., 1967. Experimental Biochemistry. p.493–495. Charles C. Thomas, Springfield.
30. Karlin, et al., 1990. Proc. Natl. Acad. Sci. USA 87:2264–2268.
31. Karlin, et al., 1993. Proc. Natl. Acad. Sci. USA 90:5873–5877.
32a. Kozel, T. R. 1977. Infect. Immun. 16:99–106.
32b. Muchmore et al., 1982, Mycopathologia 78: 41–45.
32c. Bennett et al., 1965, J. Immunol. 94: 916–920.
32d. Eng et al., 1983, Infection 11: 132–136.
33. Kozel, T. R. 1989. Antigenic structure of *Cryptococcus neoformans* capsular polysaccharides, p. 63–86. In E. Kurstak, G Marquis, P. Auger, L. de Repentigny, and S. Montplaisir (eds.), Immunology of Fungal Diseases. Marcel Dekker, Inc., New York.
34. Kozel, T. R. 1995. Trends in Microbiology 3:295–299.
35. Kozel, et al., 1971. Infect. Inmun. 3:287–294.
36. Kozel, et al., 1977. Infect. Immun. 18:701–707.
37. Kozel, et al., 1976. Infect. Immun. 14:62–67.
38. Kwon-Chung, et al., 1986. Infect. Immun. 51:218–223.
39. Levine, S. 1963. Science 139:605–606.
40. Levine, et al., 1963. J.Pathol. 42:97–117.
41. McGeoch, 1985. Virus Res. 3:271–286.
42. McPherson, et al., 1995. PCR 2: A Practical Approach. Oxford University Press, New York.
43. Mody, et al., 1993. Infect. Immun. 61:464–469.
44. Murphy, et al., 1972. Infect. Immun. 5:896–901.
45. Norris, et al., 1993. Infections in Med. 35–39.
46. Otteson, et al., 1994. J. Biol. Chem. 269:1858–1864.
47. Pettoello-Mantovani, et al., 1992. Lancet 339:21–23.
48. Price, et al., 1989. Fundamentals of Enzymology. Oxford University Press, New York.
49. Rinaldi, et al., 1986. J. Infect. Dis. 153:642
50. Sambrook, et al., 1989. Molecular Cloning. Cold Spring Harbor Laboratory Press, Cold Spring Harbor.
51. Sickles, et al., 1934. J. Bacteriol. 28:415–431.
52. Sickles, et al., 1935. Proc. Soc. Exp. Biol. Med. 32:857–858.
53. Sundstrom, et al., 1993. Infect. Immun. 61:1340–1345.
54. von Heijne, 1986. Nucleic Acids Res. 14:4683–4690.
55. von Heijne, 1989. Protein Eng. 2:531–534.
56. Watanabe, et al., 1998a. Biochim. Biophys. Acta. 1401:73–79.

57. Watanabe, et al., 1998b. Biochim. Biophys. Acta. 1401:73–79.
58. Yamaguchi, et al., 1988. Cell 53:423–432.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. Isolated and purified glucuronoxylomannan-O-acetylhydrolase coded for by DNA selected from the group consisting of:

(a) isolated DNA which encodes glucuronoxylomannan-O-acetylhydrolase;

(b) isolated DNA which hybridizes to isolated DNA of (a) above under high stringency conditions consisting of hybridization at 65° C. in 1.5×SSPE (3.0 M NaCl, 0.2 M NaH$_2$PO$_4$, 0.02 M EDTA, pH 7.4), a first wash at room temperature with 2×SSC containing 0.1% SDS and a second wash at 55° C. with 0.1×SSC containing 0.1% SDS, wherein said DNA encodes glucuronoxylomannan-O-acetylhydrolase; and (c) isolated DNA differing from the isolated DNAs of (a) and (b) above in codon sequence due to the degeneracy of the genetic code, and which encodes glucuronoxylomannan-O-acetylhydrolase.

2. The isolated and purified glucuronoxylomannan-O-acetylhydrolase of claim 1 having the amino acid sequence shown in SEQ ID No. 31.

3. A recombinant glucuronoxylomannan-O-acetylhydrolase having an amino acid sequence shown in SEQ ID No. 31.

4. The recombinant glucuronoxylomannan-O-acetylhydrolase of claim 3, wherein said glucuronoxylomannan-O-acetylhydrolase is encoded by a nucleic acid segment comprising a sequence shown in SEQ ID No. 30.

5. A kit containing purified glucuronoxylomannan-O-acetylhydrolase.

* * * * *

UNITED STATES PATENT AND TRADEMARK OFFICE
CERTIFICATE OF CORRECTION

PATENT NO. : 6,284,508 B1
DATED : September 4, 2001
INVENTOR(S) : Anne C. Savoy, Sherri L. Bloomer and Thomas R. Kozel It is certified that error appears in the above-identified patent and that said Letters Patent is hereby corrected as shown below:

Column 1,
Line 27, please start a new paragraph before the words "*C. neoformans* has".
Line 40, please insert a space between "%" and "(33)".

Column 4,
Line 45, "para-nitrophenol" should read -- para- nitrophenol --.

Column 7,
Lines 9 and 47, "et. al" should read -- et al --.
Line 27, "a t" should read -- at --.
Line 34, "Promega Is" should read -- Promega's --.
Line 42, "E Otteson" should read -- E. Otteson --.

Column 8,
Line 8, please insert a comma after "Reno".

Column 9,
Line 33, please insert a comma after "(58)".

Column 10,
Line 20, "a t" should read -- at --.

Column 13,
Line 5, please start a new paragraph before the words "The products".
Lines 15, 20 and 23, "90 minute" should read -- 90-minute --.
Line 23, please delete the word "ad".
Line 28, "30 minute" should read -- 30-minute --.
Line 35, "Go" should read -- GXM --.

Column 15,
Line 52, "a t" should read -- at --.

UNITED STATES PATENT AND TRADEMARK OFFICE
CERTIFICATE OF CORRECTION

PATENT NO.   : 6,284,508 B1
DATED        : September 4, 2001
INVENTOR(S)  : Anne C. Savoy, Sherri L. Bloomer and Thomas R. Kozel It is certified that error appears in the above-identified patent and that said Letters Patent is hereby corrected as shown below:

<ins>Column 16,</ins>
Line 64, please insert a period after the words "inverse PCR".

<ins>Columns 17 & 18,</ins>
Table 3, the third line under the heading, please move the word "sequence" over next to the word "Genomic".
Table 3, the third line under the heading, please move the DNA sequence to the left to line up with the DNA sequence above it.
Table 3, the line beginning with "Short clone", please insert a space between "C<ins>AT</ins>" and "<ins>ATG</ins>".
Table 3, please move "(SEQ ID No. 44)" to the right so that it lines up with the other sequence identifiers.
Table 3, the line beginning with "used same", please insert a space between "G<ins>GA</ins>" and "<ins>TCC</ins>".

<ins>Columns 19 and 20,</ins>
Table 3, please move "(SEQ ID No. 48)" to the right so that it lines up with the other sequence identifiers.

<ins>Column 21,</ins>
Line 34, please replace the period after "(FIG. 18)" with a semicolon.

<ins>Column 24,</ins>
Line 10, please insert a comma after "e.g.".
Line 56, "K" should read -- $K_M$ --.
Line 64, "of-these" should read -- of these --.
Line 65, please remove the period after the word "the".

<ins>Column 25,</ins>
Line 39, "short-term" should read -- short term --.

UNITED STATES PATENT AND TRADEMARK OFFICE
CERTIFICATE OF CORRECTION

PATENT NO. : 6,284,508 B1
DATED : September 4, 2001
INVENTOR(S) : Anne C. Savoy, Sherri L. Bloomer and Thomas R. Kozel It is certified that error appears in the above-identified patent and that said Letters Patent is hereby corrected as shown below:

Column 26,
Lines 2 and 4, please insert a space between "J." and "Bacteriol".
Line 7, "Clin Diagn Lab Immunol" should read -- Clin. Diagn. Lab. Immunol. --.
Line 57, please insert a period after "153:642".

Signed and Sealed this

Fifteenth Day of July, 2003

JAMES E. ROGAN
*Director of the United States Patent and Trademark Office*

SEQUENCE LISTING

```
<160> NUMBER OF SEQ ID NOS: 50

<210> SEQ ID NO 1
<211> LENGTH: 45
<212> TYPE: PRT
<213> ORGANISM: unknown
<220> FEATURE:
<223> OTHER INFORMATION: N-terminal amino acid sequence of native GXM-O-
      acetylhydrolase

<400> SEQUENCE: 1

Ala Glu Thr Ile Tyr Gln Asp Pro Val Pro Ala Gly Ala Asn Arg
                 5                  10                  15

Ala Ala Val Ala Val Pro Arg Asn Asp Trp Tyr Arg Asp Val Gln
                20                  25                  30

Asn Lys Phe Asp Lys Tyr Ser Gly Lys Pro Ala Asp Ile Val Phe
                35                  40                  45

<210> SEQ ID NO 2
<211> LENGTH: 18
<212> TYPE: PRT
<213> ORGANISM: Artificial sequence
<220> FEATURE:
<223> OTHER INFORMATION: N-terminal amino acid sequence of LysC-cleaved
      fragment of GXM-O-acetylhydrolase

<400> SEQUENCE: 2

Tyr Ser Gly Lys Pro Ala Asp Ile Val Phe Glu Gly Asp Ser Ile
                 5                  10                  15

Thr Asn Arg

<210> SEQ ID NO 3
<211> LENGTH: 20
<212> TYPE: PRT
<213> ORGANISM: Artificial sequence
<220> FEATURE:
<223> OTHER INFORMATION: N-terminal amino acid sequence of LysC-cleaved
      fragment of GXM-O-acetylhydrolase

<400> SEQUENCE: 3

Met Ile Gln Pro Asp Gly Thr Ile Ser Thr Asp Met Met Pro Asp
                 5                  10                  15

Phe Val His Pro Thr
                20

<210> SEQ ID NO 4
<211> LENGTH: 17
<212> TYPE: PRT
<213> ORGANISM: Artificial sequence
<220> FEATURE:
<223> OTHER INFORMATION: N-terminal amino acid sequence of LysC-cleaved
``` fragment of GXM-O-acetylhydrolase

<400> SEQUENCE: 4

Ile Ile Ser Arg Tyr Ala Asp Gly Asp Phe Val Ser Phe Val Asp
                5                   10                  15

Ile Ile

<210> SEQ ID NO 5
<211> LENGTH: 21
<212> TYPE: PRT
<213> ORGANISM: Artificial sequence
<220> FEATURE:
<223> OTHER INFORMATION: N-terminal amino acid sequence of LysC-cleaved
      fragment of GXM-O-acetylhydrolase

<400> SEQUENCE: 5

Glu His Phe Glu Gly Arg Ala Ala Asp Phe Gly Ile Glu Gly Asp
                5                   10                  15

Arg Val Glu Asn Ala Leu
                20

<210> SEQ ID NO 6
<211> LENGTH: 14
<212> TYPE: PRT
<213> ORGANISM: Artificial sequence
<220> FEATURE:
<223> OTHER INFORMATION: N-terminal amino acid sequence of LysC-cleaved
      fragment of GXM-O-acetylhydrolase

<400> SEQUENCE: 6

Gly Tyr Glu Ile Trp Gly Asp Ala Ile Leu Pro Ile Asn Asn
                5                   10

<210> SEQ ID NO 7
<211> LENGTH: 19
<212> TYPE: DNA
<213> ORGANISM: Artificial sequence
<220> FEATURE:
<221> NAME/KEY: primer_bind
<223> OTHER INFORMATION: nucleotide sequence of degenerate PCR primer
      N-terminal 19-mer

<400> SEQUENCE: 7
gacccggttc cggcwggyg                                              19

<210> SEQ ID NO 8
<211> LENGTH: 6
<212> TYPE: PRT
<213> ORGANISM: Artificial sequence
<220> FEATURE:
<223> OTHER INFORMATION: associated amino acid sequence of degenerate
      PCR primer N-terminal 19-mer

<400> SEQUENCE: 8

Asp Pro Val Pro Ala Gly
                5

<210> SEQ ID NO 9
<211> LENGTH: 51
<212> TYPE: DNA
<213> ORGANISM: Artificial sequence
<220> FEATURE:
<221> NAME/KEY: primer_bind
<223> OTHER INFORMATION: nucleotide sequence of degenerate PCR primer
      N-terminal 52-mer

<400> SEQUENCE: 9

```
gacccggttc cggcwggygc waaccgtgcw gcwgttgcwg twccgcgtaa c          51
```

<210> SEQ ID NO 10
<211> LENGTH: 17
<212> TYPE: PRT
<213> ORGANISM: Artificial sequence
<220> FEATURE:
<223> OTHER INFORMATION: associated amino acid sequence of degenerate
      PCR primer N-terminal 52-mer

<400> SEQUENCE: 10

Asp Pro Val Pro Ala Gly Ala Asn Arg Ala Ala Val Ala Val Pro
                 5                   10                  15
Arg Asn

<210> SEQ ID NO 11
<211> LENGTH: 21
<212> TYPE: DNA
<213> ORGANISM: Artificial sequence
<220> FEATURE:
<221> NAME/KEY: primer_bind
<223> OTHER INFORMATION: nucleotide sequence of degenerate PCR primer
      internal 21-mer "A"

<400> SEQUENCE: 11

```
rgtcgggtgw acgaagtccg g                                           21
```

<210> SEQ ID NO 12
<211> LENGTH: 21
<212> TYPE: DNA
<213> ORGANISM: Artificial sequence
<220> FEATURE:
<221> NAME/KEY: primer_bind
<223> OTHER INFORMATION: nucleotide sequence of reverse complement of
      internal 21-mer "A" primer

<400> SEQUENCE: 12

```
ccggacttcg twcacccgac y                                           21
```

<210> SEQ ID NO 13
<211> LENGTH: 7
<212> TYPE: PRT
<213> ORGANISM: Artificial sequence
<220> FEATURE:
<223> OTHER INFORMATION: associated amino acid sequence of degenerate
      PCR primer internal 21-mer "A"

<400> SEQUENCE: 13

Pro Asp Phe Val His Pro Thr
                 5

<210> SEQ ID NO 14
<211> LENGTH: 21
<212> TYPE: DNA
<213> ORGANISM: Artificial sequence
<220> FEATURE:
<221> NAME/KEY: primer_bind
<223> OTHER INFORMATION: nucleotide sequence of degenerate PCR primer
      internal 21-mer "B"

<400> SEQUENCE: 14

```
gtcrccgtcw gcgtaacggg a                                           21
```

<210> SEQ ID NO 15
<211> LENGTH: 21
<212> TYPE: DNA

```
<213> ORGANISM: Artificial sequence
<220> FEATURE:
<222> LOCATION: 12, 18
<223> OTHER INFORMATION: nucleotide sequence of reverse complement of
      internal 21-mer "B" primer

<400> SEQUENCE: 15
tcccgttacg cwgacggyga c                                              21

<210> SEQ ID NO 16
<211> LENGTH: 7
<212> TYPE: PRT
<213> ORGANISM: Artificial sequence
<220> FEATURE:
<223> OTHER INFORMATION: associated amino acid sequence of degenerate
      PCR primer internal 21-mer "B"

<400> SEQUENCE: 16

Ser Arg Tyr Ala Asp Gly Asp
              5

<210> SEQ ID NO 17
<211> LENGTH: 21
<212> TYPE: DNA
<213> ORGANISM: Artificial sequence
<220> FEATURE:
<221> NAME/KEY: primer_bind
<223> OTHER INFORMATION: nucleotide sequence of degenerate PCR primer
      internal 21-mer "C"

<400> SEQUENCE: 17
cagwgcgttt tcwacacggt c                                              21

<210> SEQ ID NO 18
<211> LENGTH: 21
<212> TYPE: DNA
<213> ORGANISM: Artificial sequence
<220> FEATURE:
<221> NAME/KEY: primer_bind
<222> LOCATION: 9, 18
<223> OTHER INFORMATION: nucleotide sequence of reverse complement of
      internal 21-mer "C" primer

<400> SEQUENCE: 18
gaccgtgtwg aaaacgcwct g                                              21

<210> SEQ ID NO 19
<211> LENGTH: 7
<212> TYPE: PRT
<213> ORGANISM: Artificial sequence
<220> FEATURE:
<223> OTHER INFORMATION: associated amino acid sequence of degenerate
      PCR primer internal 21-mer "C"

<400> SEQUENCE: 19

Asp Arg Val Glu Asn Ala Leu
              5

<210> SEQ ID NO 20
<211> LENGTH: 21
<212> TYPE: DNA
<213> ORGANISM: Artificial sequence
<220> FEATURE:
<221> NAME/KEY: primer_bind
<223> OTHER INFORMATION: nucleotide sequence of degenerate PCR primer
      internal 21-mer "D"

<400> SEQUENCE: 20
```

```
gttgttgatc ggcaggatwg c                                              21

<210> SEQ ID NO 21
<211> LENGTH: 21
<212> TYPE: DNA
<213> ORGANISM: Artificial sequence
<220> FEATURE:
<221> NAME/KEY: primer_bind
<223> OTHER INFORMATION: nucleotide sequence of reverse complement of
      internal 21-mer "D" primer

<400> SEQUENCE: 21
gcwatcctgc cgatcaacaa c                                              21

<210> SEQ ID NO 22
<211> LENGTH: 7
<212> TYPE: PRT
<213> ORGANISM: Artificial sequence
<220> FEATURE:
<223> OTHER INFORMATION: associated amino acid sequence of degenerate
      PCR primer internal 21-mer "D"

<400> SEQUENCE: 22

Ala Ile Leu Pro Ile Asn Asn
              5

<210> SEQ ID NO 23
<211> LENGTH: 29
<212> TYPE: DNA
<213> ORGANISM: Artificial sequence
<220> FEATURE:
<221> NAME/KEY: primer_bind
<223> OTHER INFORMATION: nucleotide sequence of first half 29-mer (R)
      for inverse PCR

<400> SEQUENCE: 23
ttaatgtcat ccacctgtcc cttgctcaa                                      29

<210> SEQ ID NO 24
<211> LENGTH: 29
<212> TYPE: DNA
<213> ORGANISM: Artificial sequence
<220> FEATURE:
<221> NAME/KEY: primer_bind
<223> OTHER INFORMATION: nucleotide sequence of reverse complement of
      first half 29-mer (R)

<400> SEQUENCE: 24
ttgagcaagg gacaggtgga tgacattaa                                      29

<210> SEQ ID NO 25
<211> LENGTH: 9
<212> TYPE: PRT
<213> ORGANISM: Artificial sequence
<220> FEATURE:
<223> OTHER INFORMATION: associated amino acid sequence of first half
      29-mer (R)

<400> SEQUENCE: 25

Leu Ser Lys Gly Gln Val Asp Asp Ile
              5

<210> SEQ ID NO 26
<211> LENGTH: 20
<212> TYPE: DNA
<213> ORGANISM: Artificial sequence
<220> FEATURE:
<221> NAME/KEY: primer_bind
```

```
<223> OTHER INFORMATION: nucleotide sequence of second half 20-mer (F)
      for inverse PCR

<400> SEQUENCE: 26
tcaacagcgc ggaacaaatc                                              20

<210> SEQ ID NO 27
<211> LENGTH: 7
<212> TYPE: PRT
<213> ORGANISM: Artificial sequence
<220> FEATURE:
<223> OTHER INFORMATION: associated amino acid sequence of second half
      20-mer (F)

<400> SEQUENCE: 27

Phe Asn Ser Ala Glu Gln Ile
              5

<210> SEQ ID NO 28
<211> LENGTH: 561
<212> TYPE: DNA
<213> ORGANISM: unknown
<220> FEATURE:
<223> OTHER INFORMATION: initial nucleotide sequence of the
      GXM--de-O-acetylhydrolase gene from contiguous
      alignment of PCR product sequences

<400> SEQUENCE: 28
gattggtatc gcgacgtgca gaacaaattc gacaagtaca gcggcaagcc tgccgatatc    60
gtatttgaag gggattccat caccaaccgc tgggaaggca cgggcaaagc ggtstggaag   120
gaacattttg aaggtcgtgc cgcggatttc ggmatcgagg gcgaccgcgt ggaaaatgcg   180
ttgtggcggt tgagcaaggg acaggtggat gacattaacc caaaagtggt ggtcatcatg   240
ctgggtacca ataaccccta tttcaacagc gcggaacaaa tcgcggaagg attgaagctg   300
ctggtggcgg aataccagaa acgctgtccg caggcacaca tcatcctgat gggtgttttc   360
ccgcgcggca aggacgctaa cgatggcggt cgcaagaagg ttgcggaaat caataaaatc   420
atctcccgct acgccgacgg cgacaaggta tcgttcgtgg acatcagcga caagatgatc   480
cagcccgacg gcaccatctc gaccgacatg atgccggatt tgtccatcc gaccgccaaa   540 ggctacgaga tttggggaga c                                            561

<210> SEQ ID NO 29
<211> LENGTH: 217
<212> TYPE: PRT
<213> ORGANISM: unknown
<220> FEATURE:
<223> OTHER INFORMATION: initial amino acid sequence of the
      GXM--de-O-acetylhydrolase gene obtained by peptide
      mapping

<400> SEQUENCE: 29

Ala Glu Thr Ile Tyr Gln Asp Pro Val Pro Ala Gly Ala Asn Arg
  1               5                  10                  15

Ala Ala Val Ala Val Pro Arg Asn Asp Trp Tyr Arg Asp Val Gln
                 20                  25                  30

Asn Lys Phe Asp Lys Tyr Ser Gly Lys Pro Ala Asp Ile Val Phe
                 35                  40                  45

Glu Gly Asp Ser Ile Thr Asn Arg Trp Glu Gly Thr Gly Lys Ala
                 50                  55                  60

Val Trp Lys Glu His Phe Glu Gly Arg Ala Ala Asp Phe Gly Ile
                 65                  70                  75
```

-continued

```
Glu Gly Asp Arg Val Glu Asn Ala Leu Trp Arg Leu Ser Lys Gly
             80                  85                  90

Gln Val Asp Asp Ile Asn Pro Lys Val Val Ile Met Leu Gly
         95                 100                 105

Thr Asn Asn Thr Tyr Phe Asn Ser Ala Glu Gln Ile Ala Glu Gly
                110                 115                 120

Leu Lys Leu Leu Val Ala Glu Tyr Gln Lys Arg Cys Pro Gln Ala
                125                 130                 135

His Ile Ile Leu Met Gly Val Phe Pro Arg Gly Lys Asp Ala Asn
                140                 145                 150

Asp Gly Gly Arg Lys Lys Val Ala Glu Ile Asn Lys Ile Ile Ser
                155                 160                 165

Arg Tyr Ala Asp Gly Asp Lys Val Ser Phe Val Asp Ile Ser Asp
                170                 175                 180

Lys Met Ile Gln Pro Asp Gly Thr Ile Ser Thr Asp Met Met Pro
                185                 190                 195

Asp Phe Val His Pro Thr Ala Lys Gly Tyr Glu Ile Trp Gly Asp
                200                 205                 210

Ala Ile Leu Pro Ile Asn Asn
                215
```

<210> SEQ ID NO 30
<211> LENGTH: 855
<212> TYPE: DNA
<213> ORGANISM: unknown
<220> FEATURE:
<223> OTHER INFORMATION: nucleotide sequence of GXM-O-acetylhydrolase gene

<400> SEQUENCE: 30

```
ccagtacccg gggattaatc aaatggaaaa atcatgaata aactgcatct tgtcattagc    60
gttcaactgt tagccgttgc cggttcgttg ttagcggcgg aaaccatcta tcaggatcct   120
gttccagcgg gtgccaaccg tgctgccgtt gccgtcccgc gcaacgattg gtatcgcgac   180
gtgcagaaca aattcgacaa gtacagcggc aagcctgccg atatcgtatt tgaaggggat   240
tccatcacca accgctggga aggcacgggc aaagcggtst ggaaggaaca ttttgaaggt   300
cgtgccgcgg atttcggmat cgagggcgac cgcgtggaaa atgcgttgtg gcggttgagc   360
aagggacagg tggatgacat taacccaaaa gtggtggtca tcatgctggg taccaataac   420
acctatttca acagcgcgga acaaatcgcg gaaggattga agctgctggt ggcggaatac   480
cagaaacgct gtccgcaggc acacatcatc ctgatgggtg ttttcccgcg cggcaaggac   540
gctaacgatg gcggtcgcaa gaaggttgcg gaaatcaata aaatcatctc ccgctacgcc   600
gacggcgaca aggtatcgtt cgtggacatc agcgacaaga tgatccagcc cgacggcacc   660
atctcgaccg acatgatgcc ggattttgtc catccgaccg ccaaaggcta cgagatttgg   720
ggagacgcaa tcctgccgat caacaacaaa tacgcgccga aaaataatg cgttactgcc   780
cgcggtaatt tttcgggctg gtgcccatgg ttttcttgaa tgccttggaa aacgcgaact   840
gggtcgagta ccgca                                                    855
```

<210> SEQ ID NO 31
<211> LENGTH: 244
<212> TYPE: PRT
<213> ORGANISM: unknown
<220> FEATURE:
<223> OTHER INFORMATION: amino acid sequence of GXM-O-acetylhydrolase

```
<400> SEQUENCE: 31

Met Asn Lys Leu His Leu Val Ile Ser Val Gln Leu Ala Val
                  5                  10                 15

Ala Gly Ser Leu Leu Ala Ala Glu Thr Ile Tyr Gln Asp Pro Val
                20                  25                  30

Pro Ala Gly Ala Asn Arg Ala Ala Val Ala Val Pro Arg Asn Asp
                35                  40                  45

Trp Tyr Arg Asp Val Gln Asn Lys Phe Asp Lys Tyr Ser Gly Lys
                50                  55                  60

Pro Ala Asp Ile Val Phe Glu Gly Asp Ser Ile Thr Asn Arg Trp
                65                  70                  75

Glu Gly Thr Gly Lys Ala Val Trp Lys Glu His Phe Glu Gly Arg
                80                  85                  90

Ala Ala Asp Phe Gly Ile Glu Gly Asp Arg Val Glu Asn Ala Leu
                95                 100                 105

Trp Arg Leu Ser Lys Gly Gln Val Asp Asp Ile Asn Pro Lys Val
               110                 115                 120

Val Val Ile Met Leu Gly Thr Asn Asn Thr Tyr Phe Asn Ser Ala
               125                 130                 135

Glu Gln Ile Ala Glu Gly Leu Lys Leu Leu Val Ala Glu Tyr Gln
               140                 145                 150

Lys Arg Cys Pro Gln Ala His Ile Ile Leu Met Gly Val Phe Pro
               155                 160                 165

Arg Gly Lys Asp Ala Asn Asp Gly Gly Arg Lys Lys Val Ala Glu
               170                 175                 180

Ile Asn Lys Ile Ile Ser Arg Tyr Ala Asp Gly Asp Lys Val Ser
               185                 190                 195

Phe Val Asp Ile Ser Asp Lys Met Ile Gln Pro Asp Gly Thr Ile
               200                 205                 210

Ser Thr Asp Met Met Pro Asp Phe Val His Pro Thr Ala Lys Gly
               215                 220                 225

Tyr Glu Ile Trp Gly Asp Ala Ile Leu Pro Ile Asn Asn Lys Tyr
               230                 235                 240

Ala Pro Lys Lys

<210> SEQ ID NO 32
<211> LENGTH: 229
<212> TYPE: PRT
<213> ORGANISM: Rattus norwegicus
<220> FEATURE:
<223> OTHER INFORMATION: amino acid sequence of rat ( acetylhydrolases

<400> SEQUENCE: 32

Met Ser Gln Gly Asp Ser Asn Pro Ala Ala Ile Pro His Ala Ala
                  5                  10                 15

Glu Asp Ile Gln Gly Asp Asp Arg Trp Met Ser Gln His Asn Arg
                20                  25                  30

Phe Val Leu Asp Cys Lys Asp Lys Glu Pro Asp Val Leu Phe Val
                35                  40                  45

Gly Asp Ser Met Val Gln Leu Met Gln Gln Tyr Glu Ile Trp Arg
                50                  55                  60

Glu Leu Phe Ser Pro Leu His Ala Leu Asn Phe Gly Ile Gly Gly
                65                  70                  75

Asp Thr Thr Arg His Val Leu Trp Arg Leu Lys Asn Gly Glu Leu
```

```
                    80                  85                  90
Glu Asn Ile Lys Pro Lys Val Ile Val Val Trp Val Gly Thr Asn
                    95                 100                 105

Asn His Glu Asn Thr Ala Glu Glu Val Ala Gly Gly Ile Glu Ala
                   110                 115                 120

Ile Val Gln Leu Ile Asn Thr Arg Gln Pro Gln Ala Lys Ile Ile
                   125                 130                 135

Val Leu Gly Leu Leu Pro Arg Gly Glu Lys Pro Asn Pro Leu Arg
                   140                 145                 150

Gln Lys Asn Ala Lys Val Asn Gln Leu Leu Lys Val Ser Leu Pro
                   155                 160                 165

Lys Leu Ala Asn Val Gln Leu Leu Asp Ile Asp Gly Gly Phe Val
                   170                 175                 180

His Ser Asp Gly Ala Ile Ser Cys His Asp Met Phe Asp Phe Leu
                   185                 190                 195

His Leu Thr Gly Gly Gly Tyr Ala Lys Ile Cys Lys Pro Leu His
                   200                 205                 210

Glu Leu Ile Met Gln Leu Leu Glu Glu Thr Pro Glu Glu Lys Gln
                   215                 220                 225

Thr Thr Ile Ala

<210> SEQ ID NO 33
<211> LENGTH: 229
<212> TYPE: PRT
<213> ORGANISM: Homo sapiens
<220> FEATURE:
<223> OTHER INFORMATION: amino acid sequence of human ( acetylhydrolases

<400> SEQUENCE: 33

Met Ser Gln Gly Asp Ser Asn Pro Ala Ala Ile Pro His Ala Ala
                     5                  10                  15

Glu Asp Ile Gln Gly Asp Asp Arg Trp Met Ser Gln His Asn Arg
                    20                  25                  30

Phe Val Leu Asp Cys Lys Asp Lys Glu Pro Asp Val Leu Phe Val
                    35                  40                  45

Gly Asp Ser Met Val Gln Leu Met Gln Gln Tyr Glu Ile Trp Arg
                    50                  55                  60

Glu Leu Phe Ser Pro Leu His Ala Leu Asn Phe Gly Ile Gly Gly
                    65                  70                  75

Asp Thr Thr Arg His Val Leu Trp Arg Leu Lys Asn Gly Glu Leu
                    80                  85                  90

Glu Asn Ile Lys Pro Lys Val Ile Val Val Trp Val Gly Thr Asn
                    95                 100                 105

Asn His Glu Asn Thr Ala Glu Glu Val Ala Gly Gly Ile Glu Ala
                   110                 115                 120

Ile Val Gln Leu Ile Asn Thr Arg Gln Pro Gln Ala Lys Ile Ile
                   125                 130                 135

Val Leu Gly Leu Leu Pro Arg Gly Glu Lys Pro Asn Pro Leu Arg
                   140                 145                 150

Gln Lys Asn Ala Lys Val Asn Gln Leu Leu Lys Val Ser Leu Pro
                   155                 160                 165

Lys Leu Ala Asn Val Gln Leu Leu Asp Thr Asp Gly Gly Phe Val
                   170                 175                 180

His Ser Asp Gly Ala Ile Ser Cys His Asp Met Phe Asp Phe Leu
                   185                 190                 195
```

```
His Leu Thr Gly Gly Gly Tyr Ala Lys Ile Cys Lys Pro Leu His
                200                 205                 210

Glu Leu Ile Met Gln Leu Leu Glu Glu Thr Pro Glu Glu Lys Gln
                215                 220                 225

Thr Thr Ile Ala

<210> SEQ ID NO 34
<211> LENGTH: 229
<212> TYPE: PRT
<213> ORGANISM: Mus musculus
<220> FEATURE:
<221> NAME/KEY: amino acid sequence of mouse ( acetylhydrolases

<400> SEQUENCE: 34

Met Ser Gln Gly Asp Ser Asn Pro Ala Ala Ile Pro His Ala Ala
                5                   10                  15

Glu Asp Ile Gln Gly Asp Asp Arg Trp Met Ser Gln His Asn Arg
                20                  25                  30

Phe Val Leu Asp Cys Lys Asp Lys Glu Pro Asp Val Leu Phe Val
                35                  40                  45

Gly Asp Ser Met Val Gln Leu Met Gln Gln Tyr Glu Ile Trp Arg
                50                  55                  60

Glu Leu Phe Ser Pro Leu His Ala Leu Asn Phe Gly Ile Gly Gly
                65                  70                  75

Asp Thr Thr Arg His Val Leu Trp Arg Leu Lys Asn Gly Glu Leu
                80                  85                  90

Glu Asn Ile Lys Pro Lys Val Ile Val Val Trp Val Gly Thr Asn
                95                  100                 105

Asn His Glu Asn Thr Ala Glu Glu Val Ala Gly Gly Ile Glu Ala
                110                 115                 120

Ile Val Gln Leu Ile Asn Thr Arg His Ala Gln Ala Lys Ile Ile
                125                 130                 135

Val Leu Gly Leu Leu Pro Arg Gly Glu Lys Pro Asn Pro Leu Arg
                140                 145                 150

Gln Lys Asn Ala Lys Val Asn Gln Leu Leu Lys Val Ser Leu Pro
                155                 160                 165

Lys Leu Ala Asn Val Gln Leu Leu Asp Ile Asp Gly Gly Phe Val
                170                 175                 180

His Ser Asp Gly Ala Ile Ser Cys His Asp Met Phe Asp Phe Leu
                185                 190                 195

His Leu Thr Gly Gly Gly Tyr Ala Lys Ile Cys Lys Pro Leu His
                200                 205                 210

Glu Leu Ile Met Gln Leu Leu Glu Glu Thr Pro Gly Glu Lys Gln
                215                 220                 225

Thr Thr Ile Ala

<210> SEQ ID NO 35
<211> LENGTH: 231
<212> TYPE: PRT
<213> ORGANISM: Homo sapiens
<220> FEATURE:
<223> OTHER INFORMATION: amino acid sequence of human ( acetylhydrolases

<400> SEQUENCE: 35

Met Ser Gly Glu Glu Asn Pro Ala Ser Lys Pro Thr Pro Val Gln
                5                   10                  15
```

```
Asp Val Gln Gly Asp Gly Arg Trp Met Ser Leu His His Arg Phe
             20                  25                  30

Val Ala Asp Ser Lys Asp Lys Glu Pro Glu Val Val Phe Ile Gly
             35                  40                  45

Asp Ser Leu Val Gln Leu Met His Gln Cys Glu Ile Trp Arg Glu
             50                  55                  60

Leu Phe Ser Pro Leu His Ala Leu Asn Phe Gly Ile Gly Gly Asp
             65                  70                  75

Gly Thr Gln His Val Leu Trp Arg Leu Glu Asn Gly Glu Leu Glu
             80                  85                  90

His Ile Arg Pro Lys Ile Val Val Trp Val Gly Thr Asn Asn
             95                 100                 105

His Gly His Thr Ala Glu Gln Val Thr Gly Gly Ile Lys Ala Ile
            110                 115                 120

Val Gln Leu Val Asn Glu Arg Gln Pro Gln Ala Arg Val Val Val
            125                 130                 135

Leu Gly Leu Leu Pro Arg Gly Gln His Pro Asn Pro Leu Arg Glu
            140                 145                 150

Lys Asn Arg Gln Val Asn Glu Leu Val Arg Ala Ala Leu Ala Gly
            155                 160                 165

His Pro Arg Ala His Phe Leu Asp Ala Asp Pro Gly Phe Val His
            170                 175                 180

Ser Asp Gly Thr Ile Ser His His Asp Met Tyr Asp Tyr Leu His
            185                 190                 195

Leu Ser Arg Leu Gly Tyr Thr Pro Val Cys Arg Ala Leu His Ser
            200                 205                 210

Leu Leu Leu Arg Leu Leu Ala Gln Asp Gln Gly Gln Gly Ala Pro
            215                 220                 225

Leu Leu Glu Pro Ala Pro
            230

<210> SEQ ID NO 36
<211> LENGTH: 232
<212> TYPE: PRT
<213> ORGANISM: Bos taurus
<220> FEATURE:
<223> OTHER INFORMATION: amino acid sequence of bovine
      ( acetylhydrolases

<400> SEQUENCE: 36

Met Ser Gly Asp Glu Asn Pro Ala Ser Lys Pro Thr Pro Val Gln
              5                  10                  15

Asp Val Gln Gly Asp Gly Arg Trp Met Ser Leu His His Arg Phe
             20                  25                  30

Val Ala Asp Ser Lys Asp Lys Glu Pro Glu Leu Val Phe Ile Gly
             35                  40                  45

Asp Ser Leu Val Gln Leu Met His Gln Cys Glu Ile Trp Arg Glu
             50                  55                  60

Leu Phe Ser Pro Leu His Ala Leu Asn Phe Gly Ile Gly Gly Asp
             65                  70                  75

Ser Thr Gln His Val Leu Trp Arg Leu Glu Asn Gly Glu Leu Glu
             80                  85                  90

His Ile Arg Pro Lys Ile Val Val Trp Val Gly Thr Asn Asn
             95                 100                 105

His Gly His Thr Ala Glu Gln Val Thr Gly Gly Ile Lys Ala Ile
            110                 115                 120
```

```
Val Gln Leu Val Asn Glu Arg Gln Pro Gln Ala Arg Val Val
            125                 130                 135

Leu Gly Leu Leu Pro Arg Gly Gln His Pro Asn Pro Leu Arg Glu
            140                 145                 150

Lys Asn Arg Arg Val Asn Glu Leu Val Arg Ala Ala Leu Ala Gly
            155                 160                 165

His Pro Arg Ala His Phe Leu Asp Ala Asp Pro Gly Phe Val His
            170                 175                 180

Ser Asp Gly Thr Ile Ser His His Asp Met Tyr Asp Tyr Leu His
            185                 190                 195

Leu Ser Arg Leu Gly Tyr Thr Pro Val Cys Arg Ala Leu His Ser
            200                 205                 210

Leu Leu Leu Arg Leu Leu Thr Gln Asp Gln Gly Gln Gly Gly Ala
            215                 220                 225

Pro Leu Pro Glu Pro Ser Pro
            230
```

<210> SEQ ID NO 37
<211> LENGTH: 232
<212> TYPE: PRT
<213> ORGANISM: Mus musculus
<220> FEATURE:
<223> OTHER INFORMATION: amino acid sequence of mouse ( acetylhydrolases

<400> SEQUENCE: 37

```
Met Ser Gly Glu Gly Glu Asn Pro Ala Ser Lys Pro Thr Pro Val
              5                  10                  15

Gln Asp Val Gln Gly Asp Gly Arg Trp Met Ser Leu His His Arg
             20                  25                  30

Phe Val Ala Asp Ser Lys Asp Lys Glu Pro Glu Val Val Phe Ile
             35                  40                  45

Gly Asp Ser Leu Val Gln Leu Met His Gln Cys Glu Ile Trp Arg
             50                  55                  60

Glu Leu Phe Ser Pro Leu His Ala Leu Asn Phe Gly Ile Gly Gly
             65                  70                  75

Asp Ser Thr Gln His Val Leu Trp Arg Leu Glu Asn Gly Glu Leu
             80                  85                  90

Glu His Ile Arg Pro Lys Ile Val Val Trp Val Gly Thr Asn
             95                 100                 105

Asn His Ser His Thr Ala Glu Gln Val Thr Gly Gly Ile Lys Ala
            110                 115                 120

Ile Val Gln Leu Val Asn Lys Leu Gln Pro Gln Ala Arg Val Val
            125                 130                 135

Val Leu Gly Leu Leu Pro Arg Gly Gln His Pro Asn Pro Leu Arg
            140                 145                 150

Glu Lys Asn Arg Gln Val Asn Glu Leu Val Arg Ala Ala Leu Ala
            155                 160                 165

Gly Tyr Pro Arg Ala His Phe Leu Asp Ala Asp Pro Gly Phe Val
            170                 175                 180

His Ser Asp Gly Thr Ile Ser His Asp Trp Tyr Asp Tyr Leu
            185                 190                 195

His Leu Ser Arg Leu Gly Tyr Thr Pro Val Cys Arg Ala Leu His
            200                 205                 210

Ser Leu Leu Leu Arg Leu Leu Ala Gln Asp Gln Gly Gln Gly Ile
            215                 220                 225
```

Pro Leu Pro Glu Thr Ala Ser
                230

<210> SEQ ID NO 38
<211> LENGTH: 232
<212> TYPE: PRT
<213> ORGANISM: Rattus norwegicus
<220> FEATURE:
<223> OTHER INFORMATION: amino acid sequence of rat ( acetylhydrolases

<400> SEQUENCE: 38

Met Ser Gly Glu Gly Glu Asn Pro Ala Ser Lys Pro Thr Pro Val
                 5                  10                  15

Gln Asp Val Gln Gly Asp Gly Arg Trp Met Ser Leu His His Arg
                20                  25                  30

Phe Val Ala Asp Ser Lys Asp Lys Glu Pro Glu Val Val Phe Ile
                35                  40                  45

Gly Asp Ser Leu Val Gln Leu Met His Gln Cys Glu Ile Trp Arg
                50                  55                  60

Glu Leu Phe Ser Pro Leu His Ala Leu Asn Phe Gly Ile Gly Gly
                65                  70                  75

Asp Ser Thr Gln His Val Leu Trp Arg Leu Glu Asn Gly Glu Leu
                80                  85                  90

Glu His Ile Arg Pro Lys Ile Val Val Trp Val Gly Thr Asn
                95                  100                 105

Asn His Ser His Thr Ala Glu Gln Val Thr Gly Gly Ile Lys Ala
                110                 115                 120

Ile Val Gln Leu Val Asn Lys Leu Gln Pro Gln Ala Arg Val Val
                125                 130                 135

Val Leu Gly Leu Leu Pro Arg Gly Gln His Pro Asn Pro Leu Arg
                140                 145                 150

Glu Lys Asn Arg Gln Val Asn Glu Leu Val Arg Ala Ala Leu Ala
                155                 160                 165

Gly Tyr Pro Arg Ala His Phe Leu Asp Ala Asp Pro Gly Phe Val
                170                 175                 180

His Ser Asp Gly Thr Ile Ser His His Asp Met Tyr Asp Tyr Leu
                185                 190                 195

His Leu Ser Arg Leu Gly Tyr Thr Pro Val Cys Arg Ala Leu His
                200                 205                 210

Ser Leu Leu Leu Arg Leu Leu Ala Gln Asp Gln Gly Gln Gly Ile
                215                 220                 225

Pro Leu Pro Glu Thr Ala Pro
                230

<210> SEQ ID NO 39
<211> LENGTH: 45
<212> TYPE: DNA
<213> ORGANISM: Artificial sequence
<220> FEATURE:
<223> OTHER INFORMATION: PCR primer 45-mer for expression vector

<400> SEQUENCE: 39
ggaaaacata tgaataaact gcatcttgtc attagcgttc aactg            45

<210> SEQ ID NO 40
<211> LENGTH: 45
<212> TYPE: DNA
<213> ORGANISM: Artificial sequence
<220> FEATURE:
<223> OTHER INFORMATION: genomic sequence of PCR primer 45-mer

<400> SEQUENCE: 40
ggaaaaatca tgaataaact gcatcttgtc attagcgttc aactg                    45

<210> SEQ ID NO 41
<211> LENGTH: 12
<212> TYPE: PRT
<213> ORGANISM: Artificial sequence
<220> FEATURE:
<223> OTHER INFORMATION: associated amino acid sequence of PCR primer
      45-mer

<400> SEQUENCE: 41

Met Asn Lys Leu His Leu Val Ile Ser Val Gln Leu
              5                   10

<210> SEQ ID NO 42
<211> LENGTH: 36
<212> TYPE: DNA
<213> ORGANISM: Artificial sequence
<220> FEATURE:
<223> OTHER INFORMATION: PCR primer 36-mer for expression vector

<400> SEQUENCE: 42
gttcgttgca tatggcggaa accatctatc aggatc                              36

<210> SEQ ID NO 43
<211> LENGTH: 36
<212> TYPE: DNA
<213> ORGANISM: Artificial sequence
<220> FEATURE:
<223> OTHER INFORMATION: genomic sequence of PCR primer 36-mer

<400> SEQUENCE: 43
gttcgttgtt agcggcggaa accatctatc aggatc                              36

<210> SEQ ID NO 44
<211> LENGTH: 11
<212> TYPE: PRT
<213> ORGANISM: Artificial sequence
<220> FEATURE:
<223> OTHER INFORMATION: associated amino acid sequence of primer 36-mer

<400> SEQUENCE: 44

Ser Leu Leu Ala Ala Glu Thr Ile Tyr Gln Asp
              5                   10

<210> SEQ ID NO 45
<211> LENGTH: 34
<212> TYPE: DNA
<213> ORGANISM: Artificial sequence
<220> FEATURE:
<223> OTHER INFORMATION: nucleotide sequence of PCR primer 34-mer for
      expression vector

<400> SEQUENCE: 45
gtaacggatc cttttttcgg cgcgtatttg ttga                                34

<210> SEQ ID NO 46
<211> LENGTH: 34
<212> TYPE: DNA
<213> ORGANISM: Artificial sequence
<220> FEATURE:
<223> OTHER INFORMATION: genomic sequence of PCR primer 34-mer

```
<400> SEQUENCE: 46
gtaacgcatt atttttcgg cgcgtatttg ttga                              34

<210> SEQ ID NO 47
<211> LENGTH: 34
<212> TYPE: DNA
<213> ORGANISM: Artificial sequence
<220> FEATURE:
<223> OTHER INFORMATION: reverse complement sequence of PCR primer
      34-mer

<400> SEQUENCE: 47
tcaacaaata cgcgccgaaa aaataatgcg ttac                             34

<210> SEQ ID NO 48
<211> LENGTH: 7
<212> TYPE: PRT
<213> ORGANISM: Artificial sequence
<220> FEATURE:
<223> OTHER INFORMATION: associated amino acid sequence of PCR primer
      34-mer

<400> SEQUENCE: 48

Asn Lys Tyr Ala Pro Lys Lys
                5

<210> SEQ ID NO 49
<211> LENGTH: 6
<212> TYPE: DNA
<213> ORGANISM: Artificial sequence
<220> FEATURE:
<223> OTHER INFORMATION: nucleotide sequence of NdeI restriction site

<400> SEQUENCE: 49 catatg                                                             6

<210> SEQ ID NO 50
<211> LENGTH: 6
<212> TYPE: DNA
<213> ORGANISM: Artificial sequence
<220> FEATURE:
<223> OTHER INFORMATION: nucleotide sequence of BamHI restriction site

<400> SEQUENCE: 50 ggatcc                                                             6
```